(12) United States Patent
Hillstead et al.

(10) Patent No.: US 8,647,363 B2
(45) Date of Patent: *Feb. 11, 2014

(54) ROBOTICALLY CONTROLLED HYDRAULIC END EFFECTOR SYSTEM

(75) Inventors: Richard A. Hillstead, Duluth, GA (US); Bryan D. Knodel, Flagstaff, AZ (US)

(73) Assignee: Richard A. Hillstead, Inc., Suwanee, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/612,216

(22) Filed: Sep. 12, 2012

(65) Prior Publication Data

US 2013/0006269 A1     Jan. 3, 2013

Related U.S. Application Data

(60) Continuation of application No. 13/042,019, filed on Mar. 7, 2011, now Pat. No. 8,308,757, which is a division of application No. 12/055,058, filed on Mar. 25, 2008, now Pat. No. 7,922,742, which is a division of application No. 10/990,651, filed on Nov. 17, 2004, now Pat. No. 7,503,474, which is a continuation of application No. 09/942,236, filed on Aug. 29, 2001, now Pat. No. 6,830,174.

(60) Provisional application No. 60/229,076, filed on Aug. 30, 2000.

(51) Int. Cl.
*A61B 17/3201* (2006.01)
*A61B 17/26* (2006.01)

(52) U.S. Cl.
USPC .......................................................... 606/205

(58) Field of Classification Search
USPC .................................. 606/174, 175, 205–211; 227/175.1–182.1
See application file for complete search history.

(56) References Cited

U.S. PATENT DOCUMENTS

| | | | |
|---|---|---|---|
| 2,518,994 | A | 8/1950 | Miller |
| 3,643,851 | A | 2/1972 | Green et al. |
| 4,202,479 | A | 5/1980 | Razgulov et al. |
| 4,204,623 | A | 5/1980 | Green |
| 4,207,873 | A | 6/1980 | Kruy |
| 4,290,542 | A | 9/1981 | Fedotov et al. |
| 4,349,028 | A | 9/1982 | Green |
| 4,473,077 | A | 9/1984 | Noiles et al. |

(Continued)

FOREIGN PATENT DOCUMENTS

| | | |
|---|---|---|
| EP | 0646356 | 4/1995 |
| WO | WO/97/39688 | 10/1997 |

OTHER PUBLICATIONS

International Search Report for PCT/US01/26824 dated Jan. 17, 2002.

(Continued)

*Primary Examiner* — Ryan Severson
(74) *Attorney, Agent, or Firm* — Cook Alex Ltd.

(57) ABSTRACT

A hydraulically actuated medical instrument includes an elongated shaft having proximal and distal ends, a hydraulically actuated end effector at the distal end of the shaft and a fluid flow path extending through the shaft to the end effector. The end effector may be directly manually operated by way of a handle located at the proximal end of the shaft or remotely, for example, via robotic controller. Articulation joints may be provided along the shaft, between the shaft and end effector or handle, or elsewhere. The hydraulic actuation of the present invention permits multiple axis instrument articulation, miniaturization and simplified instrument fabrication.

20 Claims, 20 Drawing Sheets

(56) References Cited

U.S. PATENT DOCUMENTS

| | | |
|---|---|---|
| 4,485,817 A | 12/1984 | Swiggett |
| 4,488,523 A | 12/1984 | Shichman |
| 4,566,620 A | 1/1986 | Green et al. |
| 4,576,167 A | 3/1986 | Noiles |
| 4,605,002 A | 8/1986 | Rebuffat |
| 4,610,383 A | 9/1986 | Rothfuss et al. |
| 4,629,107 A | 12/1986 | Fedotov et al. |
| 4,646,745 A | 3/1987 | Noiles |
| 4,671,403 A | 6/1987 | Schick |
| 4,688,555 A | 8/1987 | Wardle |
| 4,700,703 A | 10/1987 | Resnick et al. |
| 4,728,020 A | 3/1988 | Green et al. |
| 4,821,939 A | 4/1989 | Green |
| 4,869,414 A | 9/1989 | Green et al. |
| 4,880,015 A | 11/1989 | Nierman |
| 4,919,112 A | 4/1990 | Siegmund |
| 4,944,443 A | 7/1990 | Oddsen et al. |
| 4,951,861 A | 8/1990 | Schulze et al. |
| 4,962,877 A | 10/1990 | Hervas |
| 5,005,754 A | 4/1991 | Van Overloop |
| 5,018,657 A | 5/1991 | Pedlick et al. |
| 5,042,707 A | 8/1991 | Taheri |
| 5,067,964 A | 11/1991 | Richmond et al. |
| 5,174,487 A | 12/1992 | Rothfuss et al. |
| 5,197,649 A | 3/1993 | Bessler et al. |
| 5,199,627 A | 4/1993 | Christensen |
| 5,217,472 A | 6/1993 | Green et al. |
| 5,219,354 A | 6/1993 | Choudhury et al. |
| 5,222,961 A | 6/1993 | Nakao et al. |
| 5,246,156 A | 9/1993 | Rothfuss et al. |
| 5,257,713 A | 11/1993 | Green et al. |
| 5,258,006 A | 11/1993 | Rydell et al. |
| 5,258,008 A | 11/1993 | Wilk |
| 5,269,785 A | 12/1993 | Bonutti |
| 5,271,543 A | 12/1993 | Grant et al. |
| 5,289,963 A | 3/1994 | McGarry et al. |
| 5,306,234 A | 4/1994 | Johnson |
| 5,312,023 A | 5/1994 | Green et al. |
| 5,312,024 A | 5/1994 | Grant et al. |
| 5,320,269 A | 6/1994 | Deschenes et al. |
| 5,326,013 A | 7/1994 | Green et al. |
| 5,344,059 A | 9/1994 | Green et al. |
| 5,348,259 A | 9/1994 | Blanco et al. |
| 5,350,355 A | 9/1994 | Sklar |
| 5,356,064 A | 10/1994 | Green et al. |
| 5,364,002 A | 11/1994 | Green et al. |
| 5,366,479 A | 11/1994 | McGarry et al. |
| 5,376,095 A | 12/1994 | Ortiz |
| 5,381,943 A | 1/1995 | Allen et al. |
| 5,383,880 A | 1/1995 | Hooven |
| 5,392,978 A | 2/1995 | Velez et al. |
| 5,403,312 A | 4/1995 | Yates et al. |
| 5,405,073 A | 4/1995 | Porter |
| 5,405,344 A | 4/1995 | Williamson et al. |
| 5,409,498 A | 4/1995 | Braddock et al. |
| 5,411,481 A | 5/1995 | Allen et al. |
| 5,423,471 A | 6/1995 | Mastri et al. |
| 5,431,323 A | 7/1995 | Smith et al. |
| 5,439,156 A | 8/1995 | Grant et al. |
| 5,452,836 A | 9/1995 | Huitema et al. |
| 5,456,401 A | 10/1995 | Green et al. |
| 5,465,894 A | 11/1995 | Clark et al. |
| 5,470,010 A | 11/1995 | Rothfuss et al. |
| 5,478,003 A | 12/1995 | Green et al. |
| 5,482,197 A | 1/1996 | Green et al. |
| 5,484,095 A | 1/1996 | Green et al. |
| 5,485,952 A | 1/1996 | Fontayne |
| 5,497,933 A | 3/1996 | DeFonzo et al. |
| 5,522,788 A | 6/1996 | Kuzmak |
| 5,549,637 A | 8/1996 | Crainich |
| 5,560,532 A | 10/1996 | DeFonzo et al. |
| 5,562,682 A | 10/1996 | Oberlin et al. |
| 5,573,543 A | 11/1996 | Akopov et al. |
| 5,575,799 A | 11/1996 | Bolanos et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,626,587 A | 5/1997 | Bishop et al. |
| 5,626,607 A | 5/1997 | Malecki et al. |
| 5,632,432 A | 5/1997 | Schulze et al. |
| 5,634,584 A | 6/1997 | Okorocha et al. |
| 5,636,780 A | 6/1997 | Green et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,662,662 A | 9/1997 | Bishop et al. |
| 5,667,517 A | 9/1997 | Hooven |
| 5,680,982 A | 10/1997 | Schulze et al. |
| 5,690,269 A | 11/1997 | Bolanos et al. |
| 5,702,408 A | 12/1997 | Wales et al. |
| 5,704,534 A | 1/1998 | Huitema et al. |
| 5,713,505 A | 2/1998 | Huitema |
| 5,722,989 A | 3/1998 | Fitch et al. |
| 5,725,536 A | 3/1998 | Oberlin et al. |
| 5,725,556 A | 3/1998 | Moser et al. |
| 5,732,871 A | 3/1998 | Clark et al. |
| 5,743,456 A | 4/1998 | Jones et al. |
| 5,749,893 A | 5/1998 | Vidal et al. |
| 5,766,169 A | 6/1998 | Fritzsch et al. |
| 5,782,397 A | 7/1998 | Koukline |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,807,403 A | 9/1998 | Beyar et al. |
| 5,817,109 A | 10/1998 | McGarry et al. |
| 5,820,009 A | 10/1998 | Melling et al. |
| 5,823,066 A | 10/1998 | Huitema et al. |
| 5,829,662 A | 11/1998 | Allen et al. |
| 5,833,695 A | 11/1998 | Yoon |
| 5,851,214 A | 12/1998 | Larsen et al. |
| 5,855,311 A | 1/1999 | Hamblin et al. |
| 5,855,590 A | 1/1999 | Malecki et al. |
| 5,865,361 A | 2/1999 | Milliman et al. |
| 5,901,895 A | 5/1999 | Heaton et al. |
| 5,947,362 A | 9/1999 | Omli |
| 5,954,746 A | 9/1999 | Holthaus et al. |
| 6,036,706 A | 3/2000 | Morejohn et al. |
| 6,074,401 A | 6/2000 | Gardiner et al. |
| 6,099,536 A | 8/2000 | Petillo |
| 6,119,913 A | 9/2000 | Adams et al. |
| 6,139,563 A | 10/2000 | Cosgrove, III et al. |
| 6,146,394 A | 11/2000 | Morejohn et al. |
| 6,149,658 A | 11/2000 | Gardiner et al. |
| 6,149,660 A | 11/2000 | Laufer et al. |
| 6,152,894 A | 11/2000 | Kubler |
| 6,190,401 B1 | 2/2001 | Green et al. |
| 6,241,139 B1 | 6/2001 | Milliman et al. |
| 6,241,140 B1 | 6/2001 | Adams et al. |
| 6,241,740 B1 | 6/2001 | Davis et al. |
| 6,250,532 B1 | 6/2001 | Green et al. |
| 6,264,086 B1 | 7/2001 | McGuckin, Jr. |
| 6,270,516 B1 | 8/2001 | Tanner et al. |
| 6,273,902 B1 | 8/2001 | Fogarty et al. |
| 6,273,903 B1 | 8/2001 | Wilk |
| 6,302,311 B1 | 10/2001 | Adams et al. |
| 6,312,437 B1 | 11/2001 | Kortenbach |
| 6,315,715 B1 | 11/2001 | Taylor et al. |
| 6,330,965 B1 | 12/2001 | Milliman et al. |
| 6,368,341 B1 | 4/2002 | Abrahamson |
| 6,460,749 B1 | 10/2002 | Levinson et al. |
| 6,464,703 B2 | 10/2002 | Bartel |
| 6,471,709 B1 | 10/2002 | Fawzi et al. |
| 6,500,115 B2 | 12/2002 | Krattiger et al. |
| 6,503,194 B2 | 1/2003 | Pauker |
| 6,527,786 B1 | 3/2003 | Davis et al. |
| 6,607,475 B2 | 8/2003 | Doyle et al. |
| 6,619,529 B2 | 9/2003 | Green et al. |
| 6,644,532 B2 | 11/2003 | Green et al. |
| 6,723,087 B2 | 4/2004 | O'Neill et al. |
| 6,743,239 B1 | 6/2004 | Kuehn et al. |
| 6,755,338 B2 | 6/2004 | Hahnen |

(56) References Cited

U.S. PATENT DOCUMENTS

| | | |
|---|---|---|
| 6,830,174 B2 | 12/2004 | Hillstead et al. |
| 6,835,199 B2 | 12/2004 | McGuckin, Jr. et al. |
| 6,978,921 B2 | 12/2005 | Shelton, IV et al. |
| 6,981,628 B2 | 1/2006 | Wales |
| 7,000,818 B2 | 2/2006 | Shelton, IV et al. |
| 7,090,684 B2 | 8/2006 | McGuckin, Jr. et al. |
| 7,246,734 B2 | 7/2007 | Shelton, IV |
| 7,470,268 B2 | 12/2008 | Doyle et al. |
| 7,503,474 B2 | 3/2009 | Hillstead et al. |
| 7,922,742 B2 | 4/2011 | Hillstead et al. |
| 8,308,757 B2 | 11/2012 | Hillstead et al. |
| 8,480,741 B2 | 7/2013 | Grotz |
| 2001/0018553 A1 | 8/2001 | Krattiger et al. |
| 2001/0030219 A1 | 10/2001 | Green et al. |
| 2001/0041893 A1 | 11/2001 | Bartel |
| 2001/0053874 A1 | 12/2001 | Pauker |
| 2002/0004663 A1 | 1/2002 | Gittings et al. |
| 2003/0045900 A1 | 3/2003 | Hahnen et al. |
| 2005/0107824 A1 | 5/2005 | Hillstead et al. |
| 2007/0102473 A1 | 5/2007 | Shelton, IV et al. |

OTHER PUBLICATIONS

International Search Report for PCT/US03/16377 dated Oct. 15, 2003.

Supplemental EP Search Report for EP Application No. EP 01968199.8 dated May 17, 2006.

U.S. Appl. No. 60/219,593, filed Jul. 20, 2000, Mark Christopher Doyle.

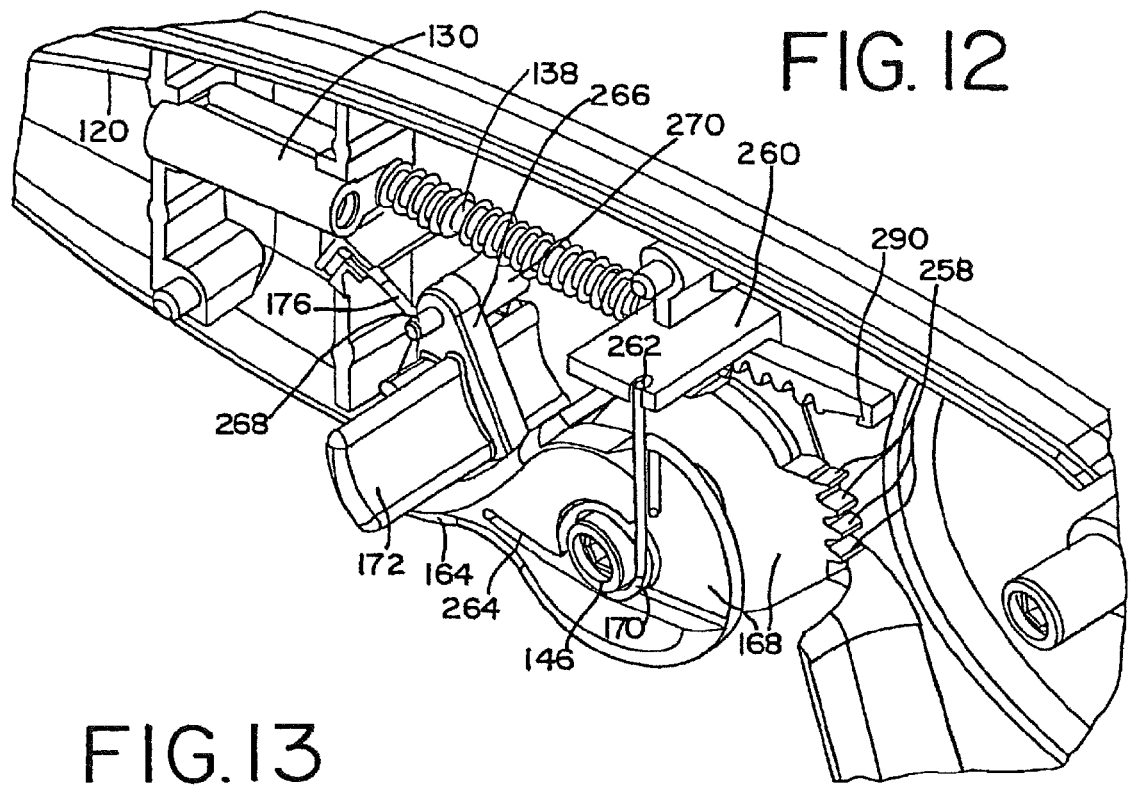
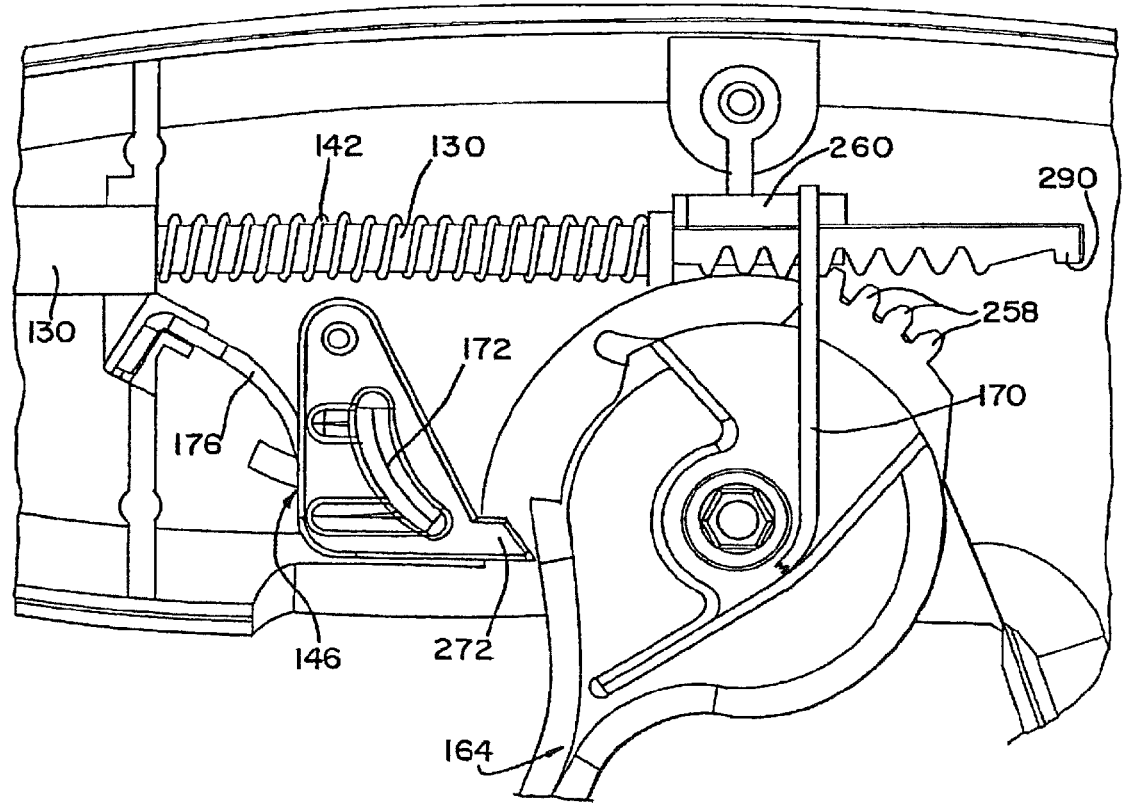

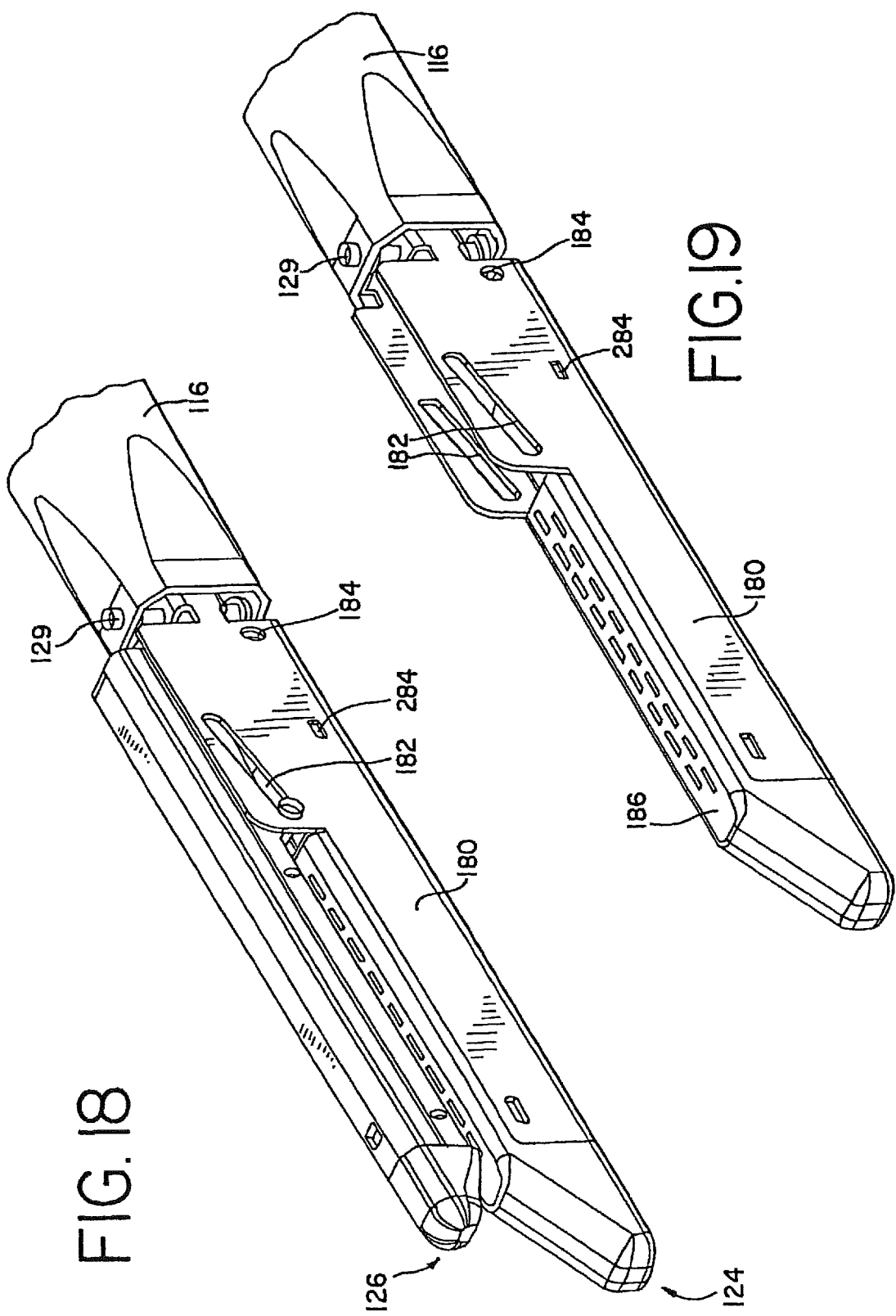

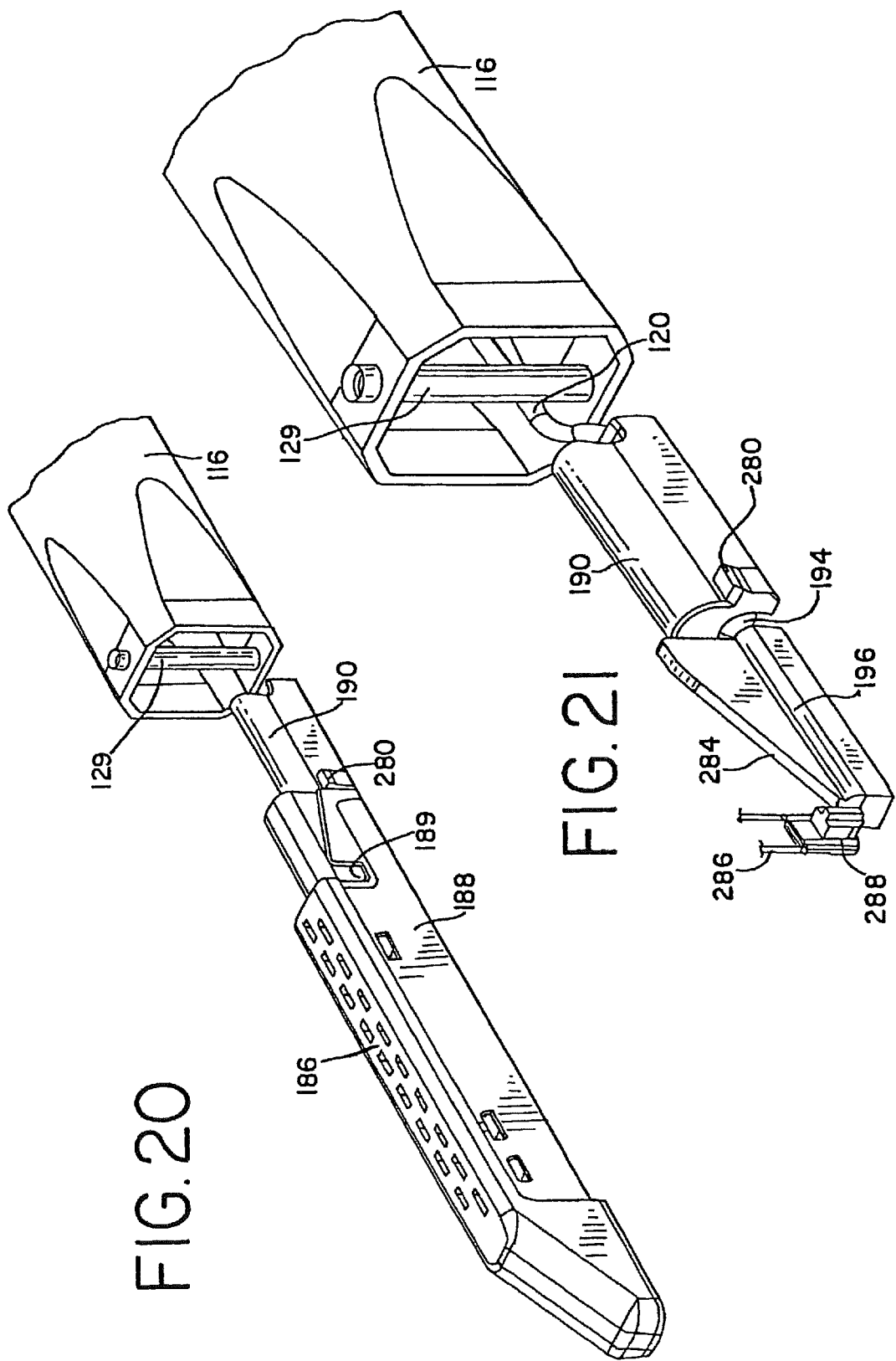

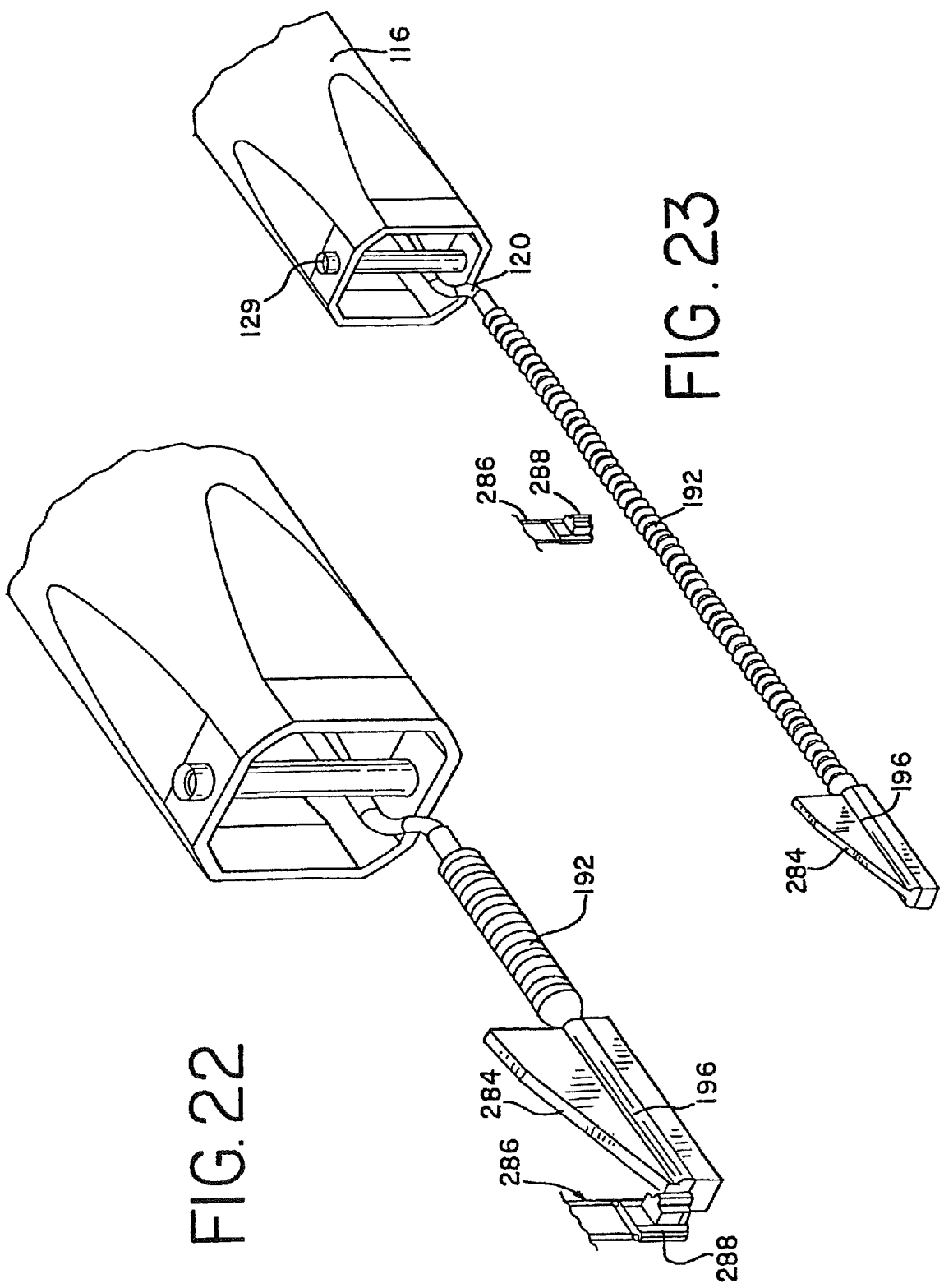

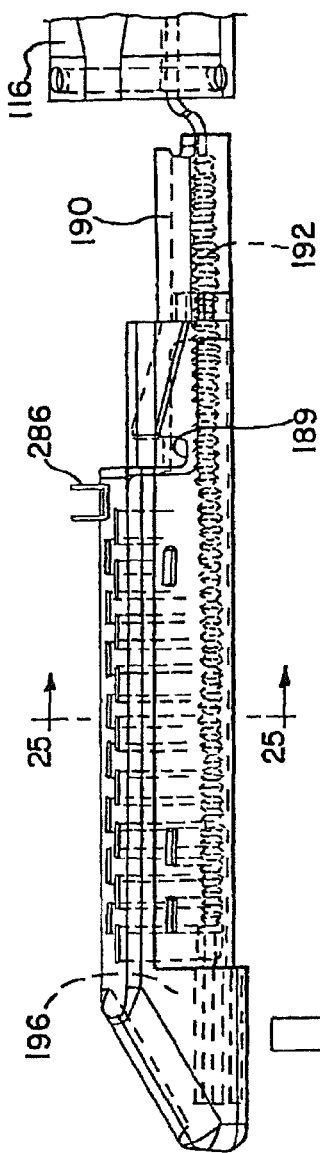
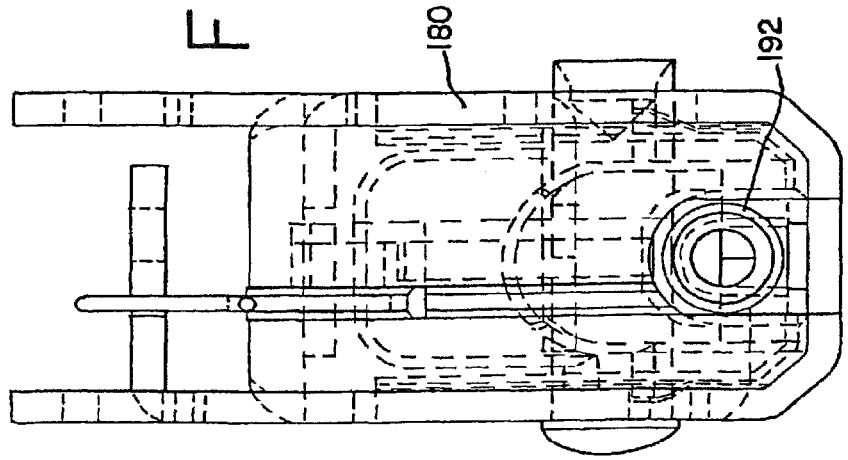
FIG. 24
FIG. 25

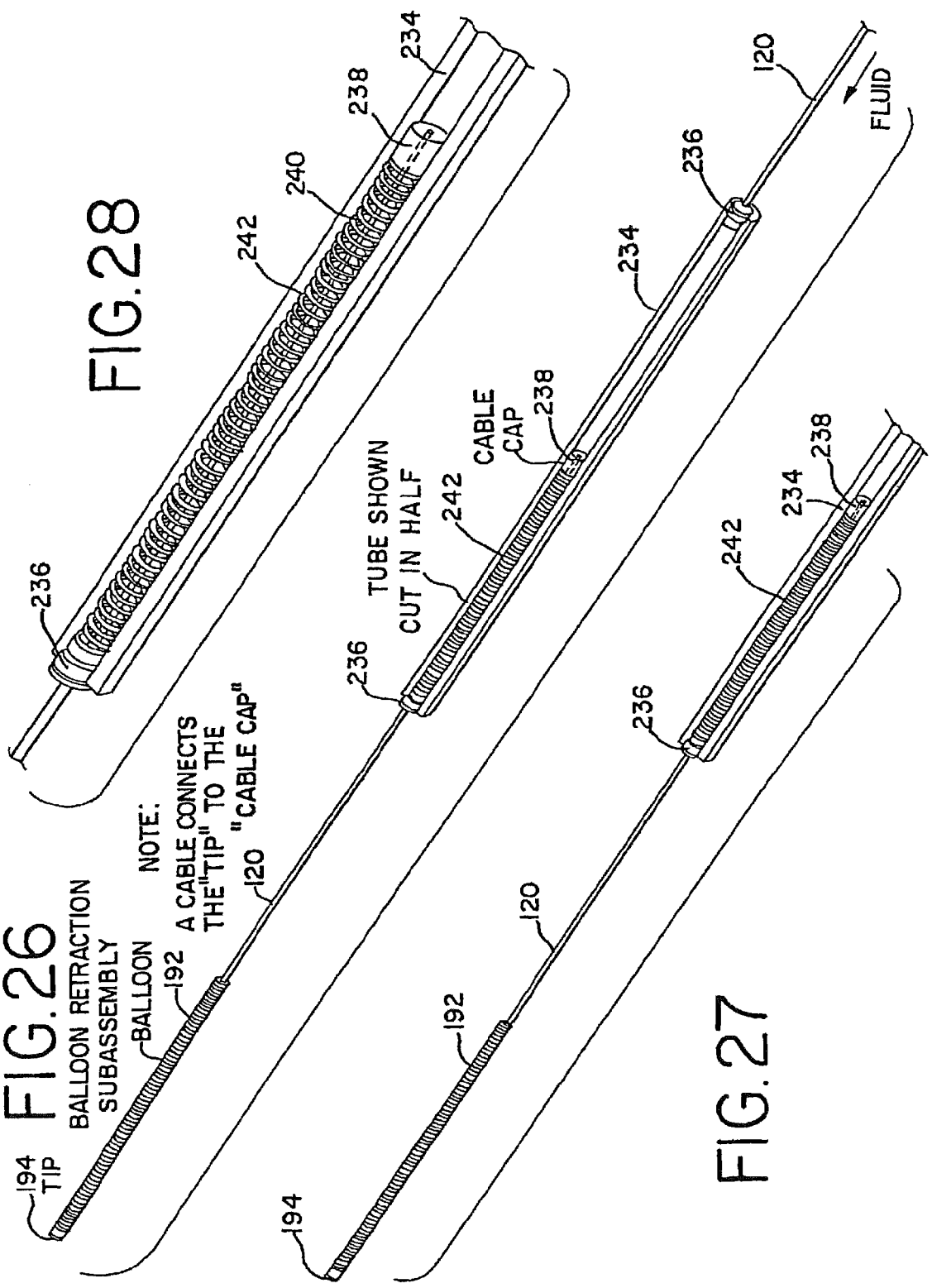

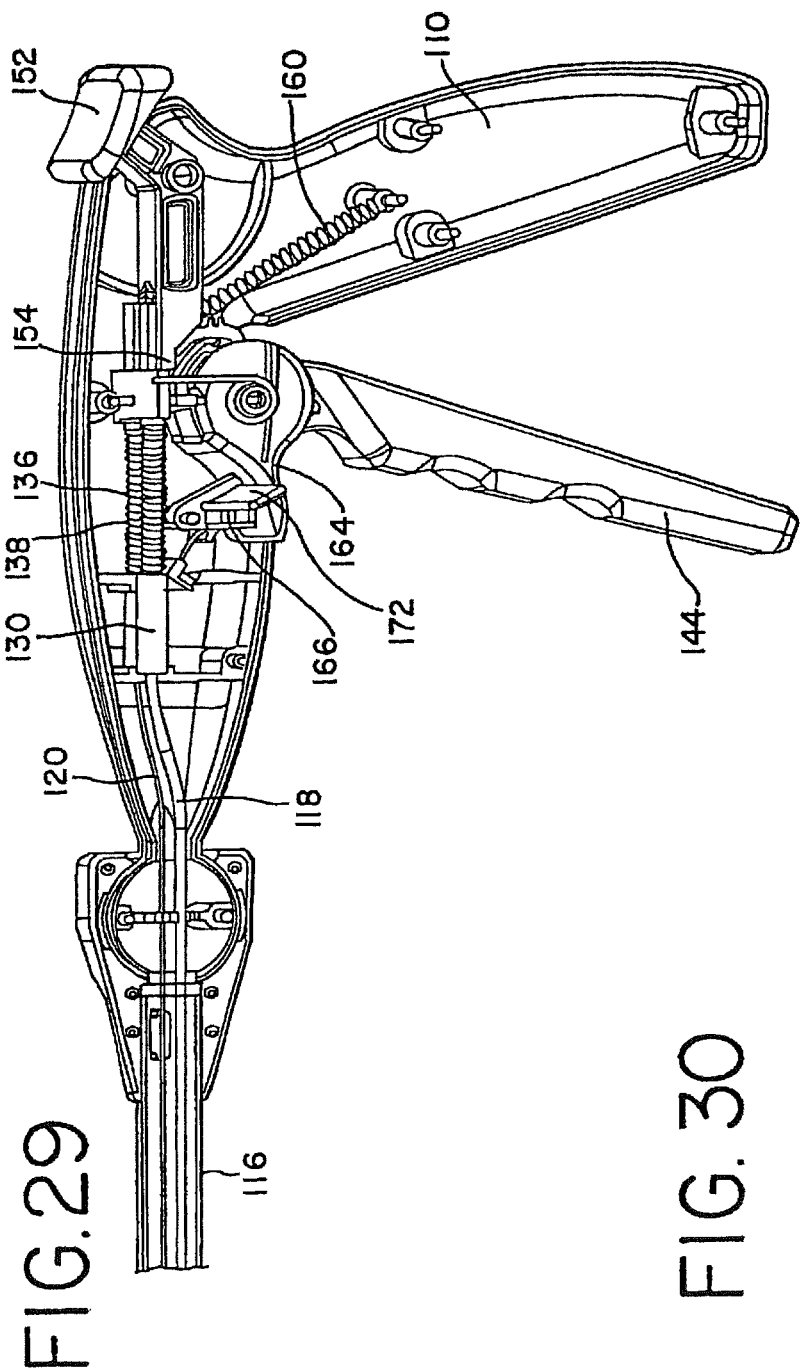
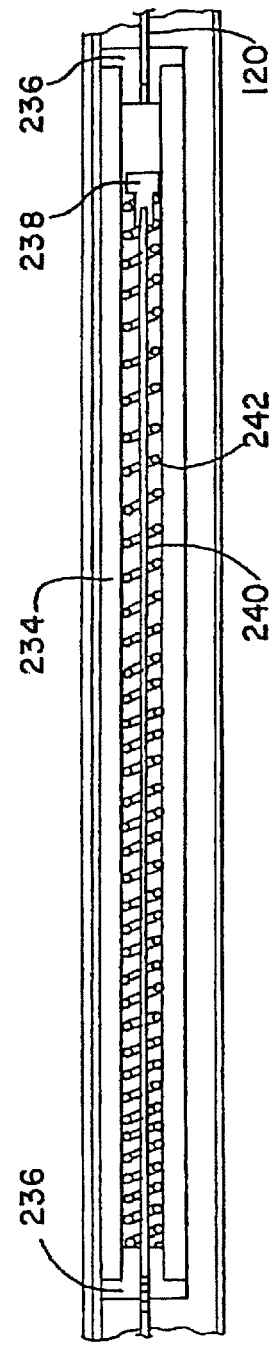
FIG. 29
FIG. 30

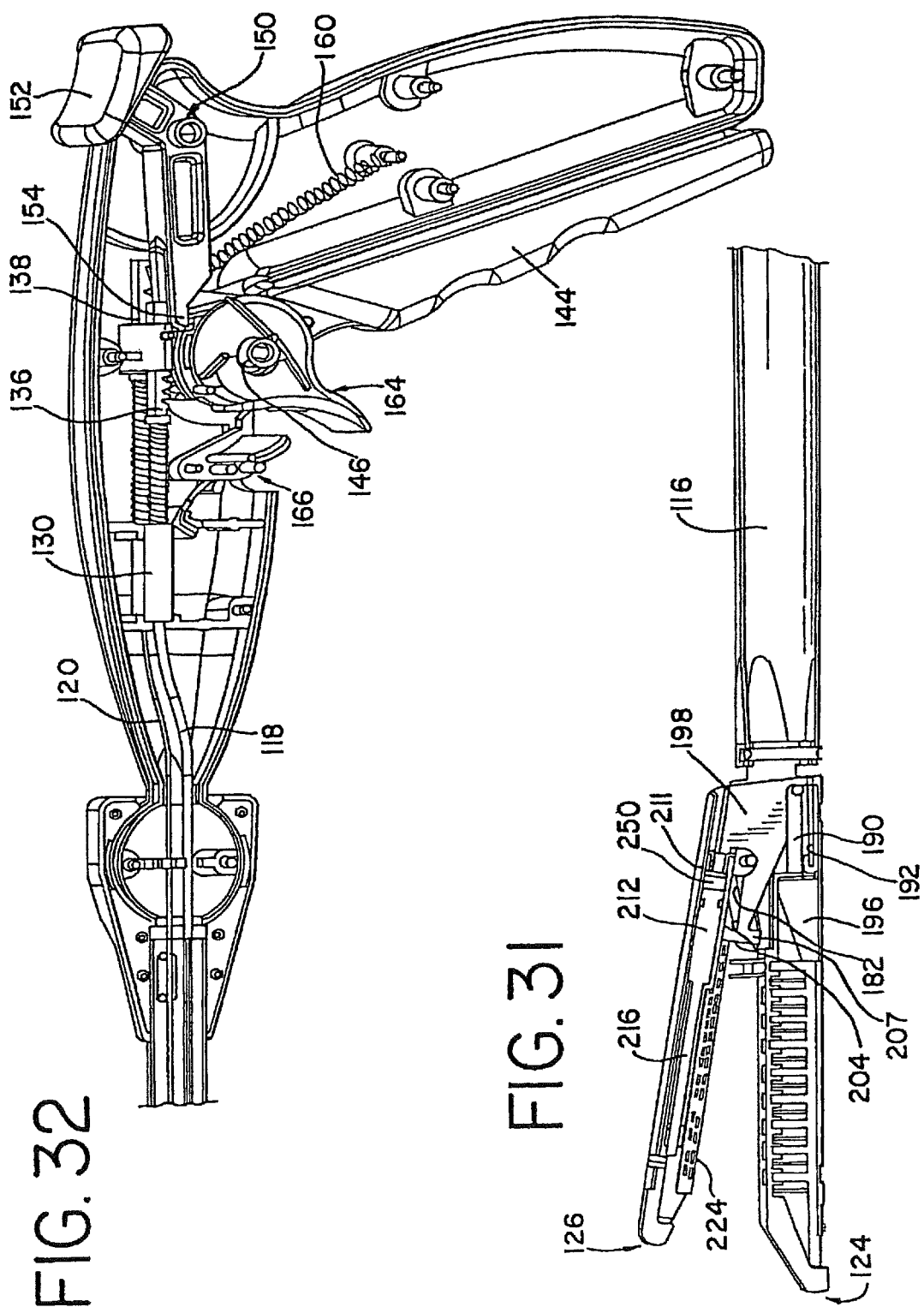

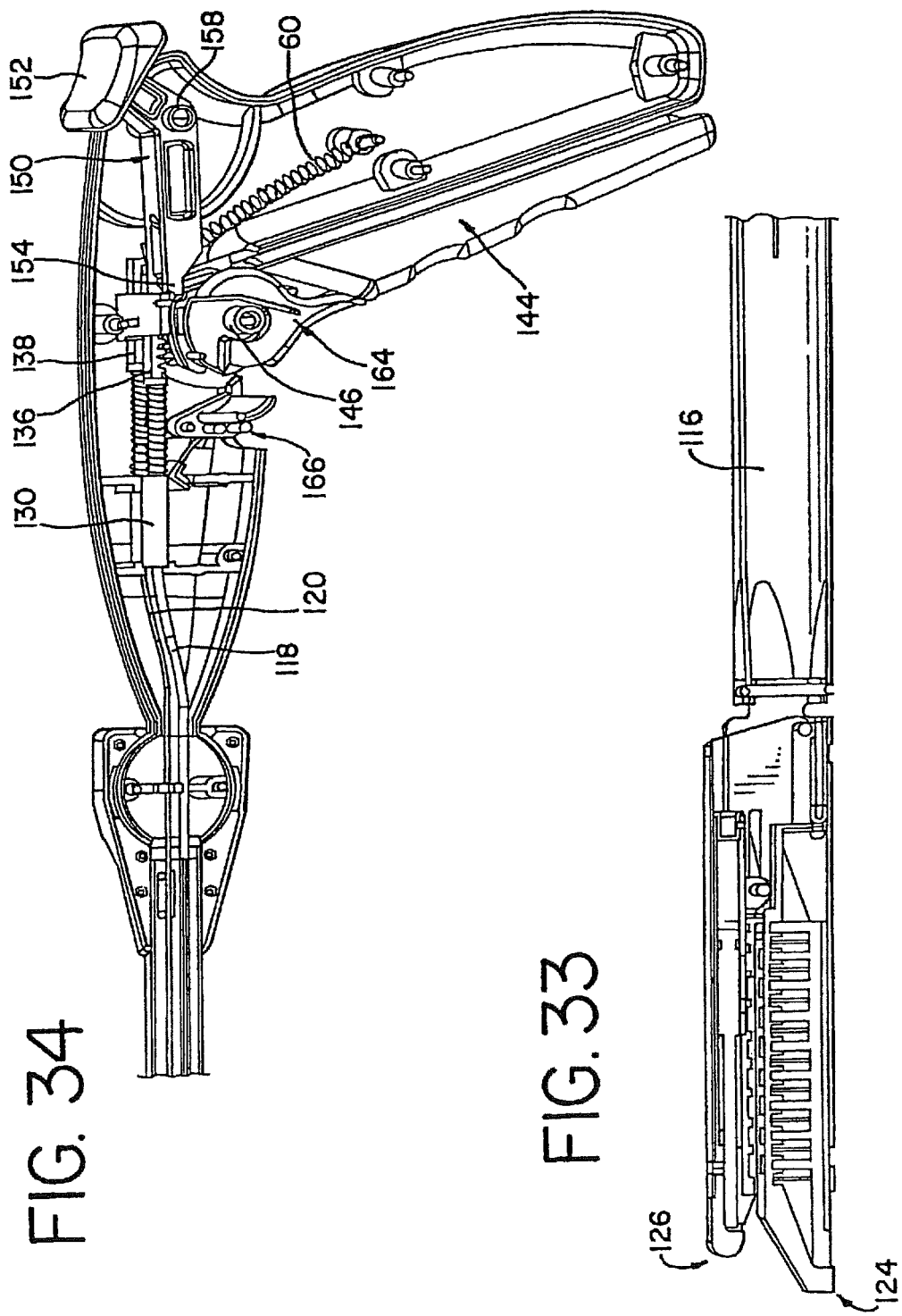

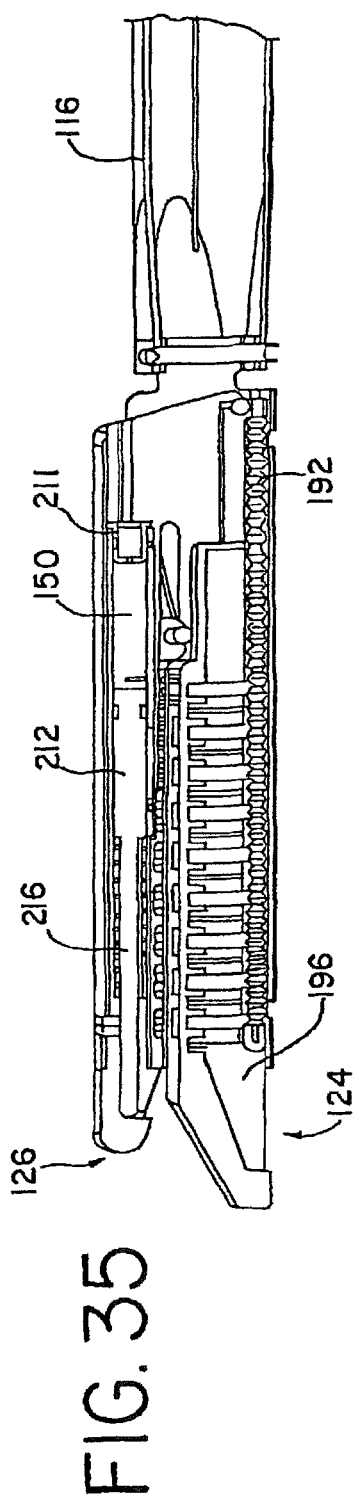
FIG. 35
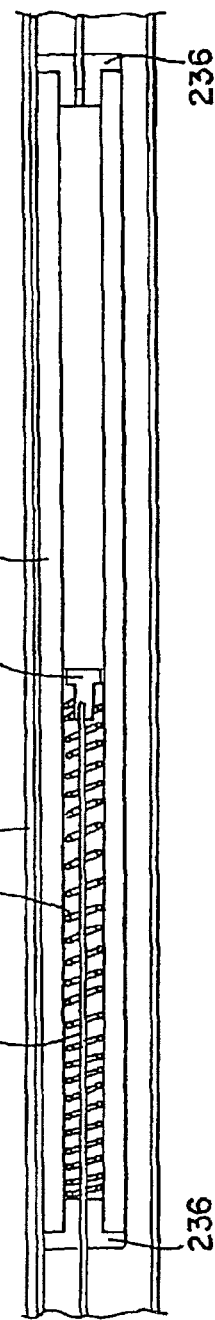
FIG. 36
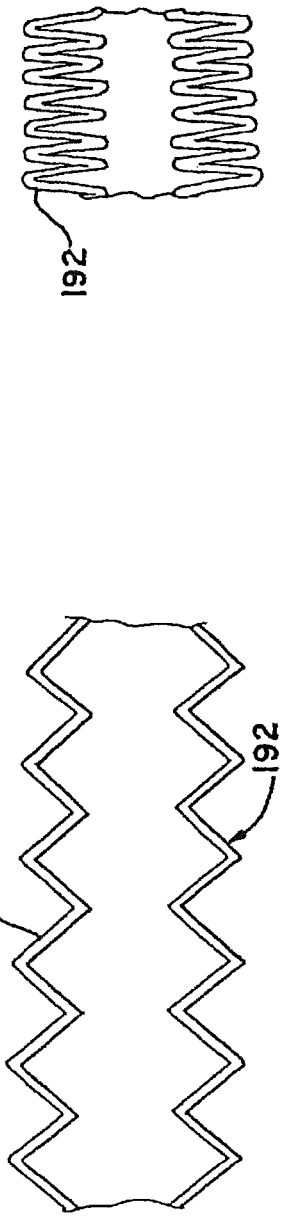
FIG. 37 (EXTENDED, INFLATED POSITION)
FIG. 38 (RETRACTED, DEFLATED POSITION)

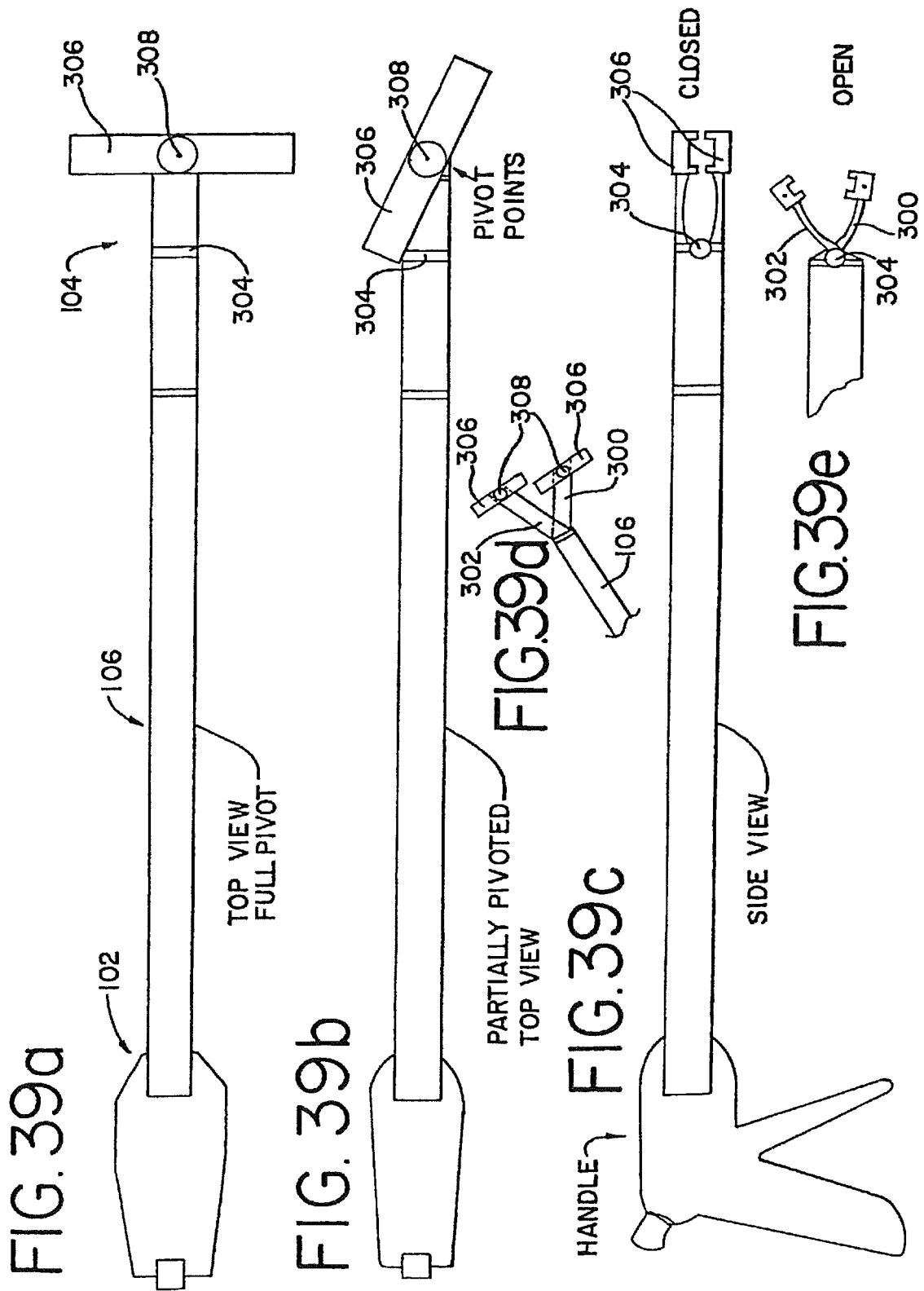

ROBOTICALLY CONTROLLED HYDRAULIC END EFFECTOR SYSTEM

PRIORITY CLAIM

This application is a continuation of U.S. application Ser. No. 13/042,019 filed Mar. 7, 2011, now U.S. Pat. No. 8,308,757, which is a divisional application of U.S. application Ser. No. 12/055,058, filed Mar. 25, 2008, now U.S. Pat. No. 7,922,742 which is a divisional application of U.S. application Ser. No. 10/990,651, filed Nov. 17, 2004 now U.S. Pat. No. 7,503,474, which is a continuation of application Ser. No. 09/942,236, filed on Aug. 29, 2001, now U.S. Pat. No. 6,830,174, which claims the benefit of provisional application Ser. No. 60/229,076, filed Aug. 30, 2000. Each of the above applications is hereby incorporated by reference.

BACKGROUND OF THE INVENTION

The present invention relates in general to medical instruments suitable for endoscopic or laproscopic applications, and capable of passing through a trocar or similar device. More specifically, the present invention relates to a novel hydraulically actuated medical instrument suitable for stapling or other desired endoscopic or laproscopic applications.

Surgical instruments, such as staplers, graspers, scissors, coagulators and the like, suitable for endoscopic or laproscopic applications in which the device is inserted through a cannula or trocar, are well known. As described in more detail below, the present invention, in its most preferred embodiment, is directed to an endoscopic stapler particularly suited for minimally invasive surgery for isolating the left atrial appendage on human hearts.

In U.S. Pat. No. 5,306,234, incorporated by reference herein, Dr. W. Dudley Johnson described a minimally invasive procedure for isolating the left atrial appendage of the human heart from the associated atrium. It is known that during atrial fibrillation blood may pool in the left atrial appendage. When blood pools in the atrial appendage, clots may form. Upon the resumption of normal beating, these clots may be ejected from the appendage and enter the blood flow to other parts of the body. If the clots enter the arteries of the brain or heart, stroke or heart attack may result.

In his patent, Dr. Johnson described a procedure for isolating the left atrial appendage without requiring open heart surgery, as was previously used. Specifically, he described entering the chest cavity between selected ribs with a minimally invasive opening or openings, while maintaining the sternum and ribs intact. While this procedure holds great promise, there remains a need for instruments suitable for conveniently and efficiently carrying out this procedure. The present invention provides such an instrument, although it also has aspects and features not limited to the particular procedure described in Dr. Johnson's patent or to stapling apparatus procedures in general.

Also, endoscopic medical instruments are often of complicated construction, especially when the instrument is articulated to allow the handle and/or end effector to pivot or rotate. Typically, a mechanical linkage extends between the handle and end effector to allow operator actuation of the end effector. When the instrument is of the type that permits articulation, the mechanical linkage must accommodate the articulation. This often results in a design that is relatively complicated, that is costly to manufacture and/or that may still experience limitations regarding the degree or direction of articulation.

SUMMARY OF THE CLAIMED INVENTION

The present invention is generally embodied in a medical device of a type suitable for endoscopic or laproscopic procedures and which includes, in one embodiment, an elongated shaft having a proximal end and a distal end, an end effector at the distal end of the elongated shaft, and a handle portion at the proximal end of the elongated shaft. In accordance with the present invention, the end effector is hydraulically actuated and at least one hydraulic fluid flow path extends between the handle portion and the end effector through the elongated shaft.

In accordance with another aspect of the present invention, the medical instrument may include at least one articulation joint at a selected location in or between the handle portion and the end effector. The articulation joint may be located between the elongated shaft and the handle portion, between the elongated shaft and the end effector or elsewhere along the shaft or within the handle or end effector if so desired. More than one articulation joint may be provided to allow greater motion options and to make the instrument particularly well suited to carry out the atrial appendage isolation procedure described above. For that purpose, the end effector is preferably biased in a lateral direction to specially position it for the atrial appendage procedure. It should be noted, however, that although the present invention is described below in terms of a device particularly well suited for the atrial appendage isolation procedure, it includes aspects or features that are not limited to the particular illustrated device or to that particular procedure.

A benefit of the present invention in its preferred embodiment is that the degree and direction of articulation are essentially unlimited. To allow articulation while providing fluid communication between the handle and end effector, at least the portion of the hydraulic fluid flow path in proximity to the articulation joint is flexible. More specifically, the fluid flow path may be flexible along its entire length or may be rigid in certain areas and flexible in proximity to the articulation joint to provide fluid flow communication along the flow path without substantially impairing articulation.

The present invention is particularly advantageous in a medical instrument having an end effector that has multiple motions or operations, Such a medical instrument may comprise a plurality (2, 3 or more) of independent closed hydraulic fluid flow paths extending between the handle portion and the end effector, which each flow path controlling a different operation or movement.

Where the end effector is for stapling tissue, for example, it may have a pair of relatively movable jaws, and a pair of hydraulic actuators—one for opening and/or closing the jaws and one for firing the staples. In such an embodiment, a pair of independent closed hydraulic flow paths may extend between the handle and the end effector, and the handle portion may include a separate hydraulic pressure source communicating with each fluid flow path. Each pressure source is controllable by the user for changing the hydraulic pressure within each of the flow paths for selective actuation of the end effector.

In such a medical instrument, the use of flexible hydraulic systems for end effector actuation is of substantial advantage, particularly in combination with multiple articulation joints. The complicated structures and relationships that would be required for direct mechanical control mechanisms through the articulation joints are essentially eliminated, and the instrument fabrication can be greatly simplified and miniaturized.

Although the present invention may be used with a variety of end effectors, tissue stapling is one of its anticipated uses. For tissue stapling, the instrument preferably employs a dual-hydraulic system for controlling the action of the end effector. For example, as a stapler, one closed hydraulic system is employed for opening and/or closing the stapler jaws, and a separate and independent closed hydraulic system is employed to effect the stapling operation.

The end effector preferably includes a plurality of staples carried by one jaw and a staple anvil carried by the other jaw. The staples may be contained in a removable supply cartridge and the hydraulic actuator may be adapted to force the staples from the respective jaw and against the anvil of the other jaw. To effect firing of the staples, the end effector may have a linearly extensible balloon engageable with a movable staple ejector, such as a cam or wedge, to forcibly expel the staples from the jaw upon increase of hydraulic pressure in the balloon. The staples are expelled with enough force to bend over the ends of the staples when they engage against the anvil to clinch tissue that is clamped between the stapler jaws. After the stapling action is complete, the balloon is positively mechanically returned to a retracted or deflated position for the next stapling operation. For purposes of the remainder of this description and any claims, "balloon" is intended to be given a broad generic interpretation that comprehends any device expansible under hydraulic pressure, whether a flexible resilient member or otherwise.

To effect opening and closing of the jaws of the end effector, the end effector may include another hydraulic actuator employing a novel piston-cylinder arrangement substantially fully enclosed in the anvil jaw of the end effector. The actuator employs a longitudinally moveable piston and a connecting linkage associated with the piston and cooperative with each of the first and second jaws to move them toward one another upon increase of hydraulic pressure in the hydraulic actuator. Preferably, the jaws are biased to an open position, such as by a spring, and upon the release of hydraulic pressure the jaws would automatically open.

To control jaw clamping, the pressure source in the handle communicating with the jaw closing actuator may be a hydraulic cylinder block communicating with the relevant hydraulic fluid flow path. To change the pressure of the hydraulic fluid, a piston is slidably movable within the cylinder block between at least a higher pressure position and a lower pressure position. The piston may be moved by a lever that is pivotally mounted on the handle portion and engageable with the piston so that operator actuation of the lever directly changes the hydraulic fluid pressure.

The medical instrument may further include a trigger cooperative with one of the pressure sources for changing the hydraulic pressure source in one of the fluid flow paths. As with the lever, the trigger may operate on a piston slidably received in a cylinder block (which may be separate from or one-piece with cylinder block employed by the lever-actuated piston) for changing the pressure in one of the hydraulic flow paths. In a stapling instrument, the trigger may operate to effect the stapling function after the end effector jaws are closed by the lever. A safety latch engageable with the trigger holds the trigger in a lower pressure, retracted and inaccessible position until the jaws are closed and locked in the desired position. The safety may then be released, and the trigger deployed, by a positive deliberate action by the surgeon. When the trigger is pulled—the hydraulic pressure in the fluid flow path is increased, causing the balloon to expand, forcing a wedge or cam forward, and causing staples to be forced from one jaw and against an anvil on the other jaw.

In accordance with a preferred aspect of the present invention, the separate clamping and firing hydraulic systems of the stapler employ a common, one-piece cylinder block. In combination with a unique firing trigger and clamping lever arrangement and piston arrangement, a compact and efficient handle arrangement that is easy to assemble and includes several built-in safety features, as discussed below, is provided.

Other aspects of the present invention, as set forth in the following detailed description and claims, are found in the end effector assembly and in the handle portion alone. Although described in terms of a complete instrument suitable for insertion through a trocar or the like, various features of the present invention found in the end effector and in the handle portion may have application in other instruments and with different style handles and end effectors without departing from the present invention.

DESCRIPTION OF DRAWINGS

FIG. 12 is a perspective view of the handle of FIG. 11, taken from a different angle, showing the safety latch and the firing trigger in the undeployed, retracted position.

FIG. 13 is an enlarged side view of the handle of FIG. 11, and of the firing trigger and safety latch in particular, with the firing trigger in the deployed position.

FIG. 18 is a perspective view of the end effector jaws of the instrument of FIG. 1 in the closed position.

FIG. 19 is a perspective view of the lower end effector jaw of the present invention in FIG. 18, with the upper jaw removed.

FIG. 20 is a perspective view of the lower jaw of the end effector, with portions removed as compared to FIG. 19 for better illustration.

FIG. 21 is a perspective view of portions of the lower end effector jaw, with portions removed as compared to FIG. 20 for better illustration.

FIG. 22 is a perspective view of portions of the lower end effector jaw with portions removed as compared to FIG. 21 for better illustration.

FIG. 23 is a perspective view of portions of the lower end effector jaw, comparable to FIG. 22, but with the balloon expanded to illustrate the balloon position after staple firing.

FIG. 24 is a side view of the lower end effector jaw after staple firing.

FIG. 25 is a vertical cross-sectional view taken along lines 25-25 of FIG. 24.

FIG. 26 is a perspective view of a portion of the balloon retraction assembly of the instrument of FIG. 1 for retracting the balloon after staple firing.

FIG. 27 is an enlarged view of a portion of the distal portion of FIG. 26, for better illustration of the balloon and parts of the balloon retraction assembly.

FIG. 28 is a further enlarged view of a portion of the balloon retraction of assembly of FIG. 26.

FIG. 29 is an enlarged cross-sectional view of the handle portion and first articulation joint connecting the handle portion to the barrel portion of the instrument shown in FIG. 1, with the jaws of the end effector in an open position.

FIG. 30 is a cross-sectional view of a barrel portion of the instrument of FIG. 1, illustrating a portion of the mechanism for positively retracting the actuator balloon after staple firing. The position indicated in FIG. 30 is the position with the balloon fully retracted before staple firing.

FIG. 31 is an enlarged cross-sectional view of the end effector portion and distal end of the barrel portion of the instrument of FIG. 1 showing the jaws in the fully open position.

FIG. 32 is an enlarged cross-sectional view of the handle portion and first articulation joint or gimbal connecting the handle portion to the barrel portion of the instrument shown in FIG. 1 with the jaws of the end effector in a closed position.

FIG. 33 is an enlarged cross-sectional view of the end effector portion and distal end of the barrel portion of the instrument of FIG. 1 showing the jaws in the fully clamped position.

FIG. 34 is an enlarged cross-sectional view of the handle portion and first articulation joint or gimbal connecting the handle portion to the barrel portion of the instrument shown in FIG. 1 with the jaws of the end effector in a closed position and the staples fired FIG. 35 is an enlarged cross-sectional view of the end effector portion and distal end of the barrel portion of the instrument of FIG. 1 showing the jaws in the fully clamped position and staples fired.

FIG. 36 is a cross-sectional view of a barrel portion of the instrument of FIG. 1, illustrating a portion of the mechanism for positively retracting the actuator balloon after staple firing. The position indicated in FIG. 36 is the position with the balloon expanded to its full length after staple firing.

FIGS. 37 and 38 are cross-sectional views, respectively, of the staple actuation balloon in the inflated and deflated condition.

FIG. 39a is a top view of an instrument of the present invention employing distal jaws that are pivotable in different directions, and showing the jaws pivoted at a right angle to the barrel.

FIG. 39b is a top view of the instrument of FIG. 39a with the jaws pivoted at less than 90° to the barrel.

FIG. 39c is a side view of the instrument of FIG. 39a with the jaws closed.

FIG. 39d is a perspective view of the distal end of the instrument of FIG. 39b.

FIG. 39e is a side view of the distal end of the instrument of FIG. 39c with the jaws open.

DESCRIPTION OF ILLUSTRATED INSTRUMENT

Figure 1:
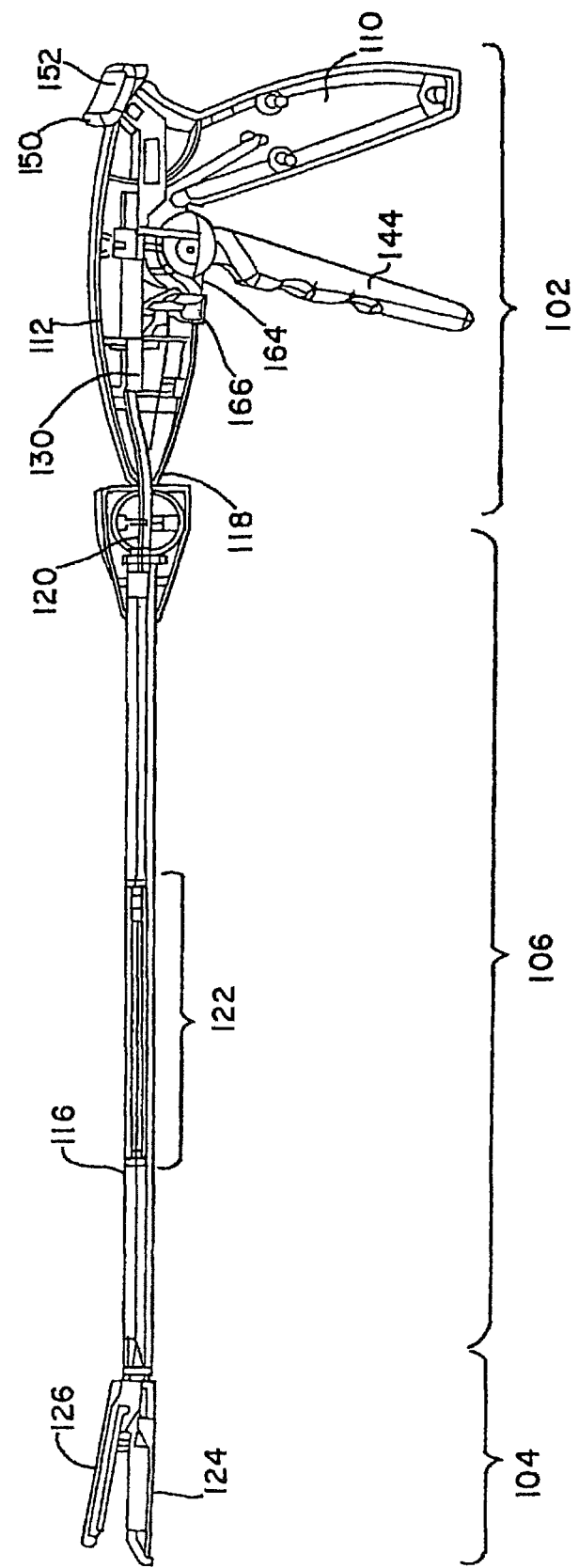
FIG. 1 is vertical cross-sectional view of an endoscopic stapling instrument employing the various features and aspects of the present invention. This figure shows the handle assembly, barrel or shaft assembly and end effector assembly. This cross-sectional view is slightly tilted toward the viewer to provide a slightly downward perspective.
Figure 2:
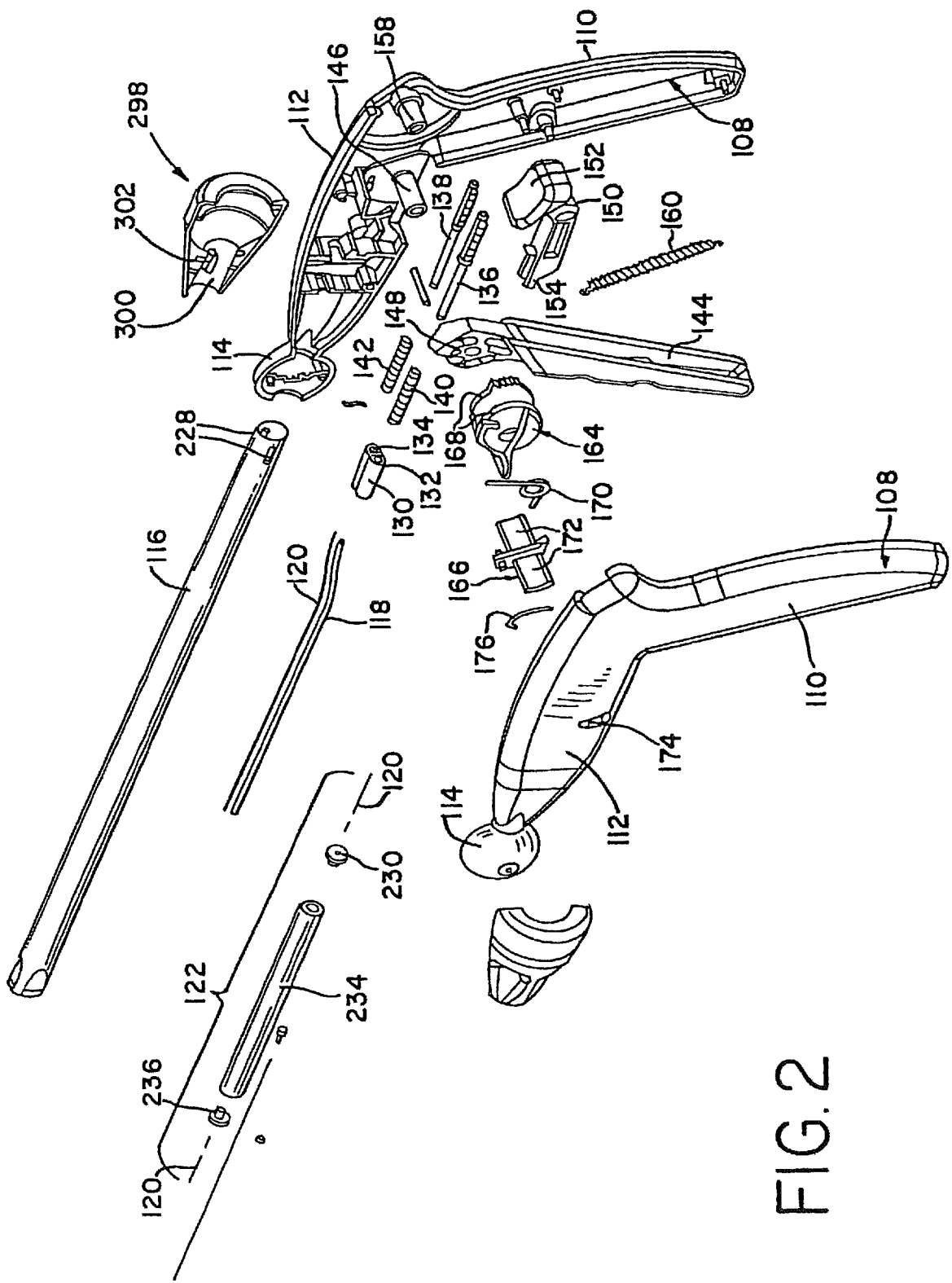
FIG. 2 is an exploded perspective view of the handle assembly and the barrel assembly of the instrument of FIG. 1.
Figure 3:
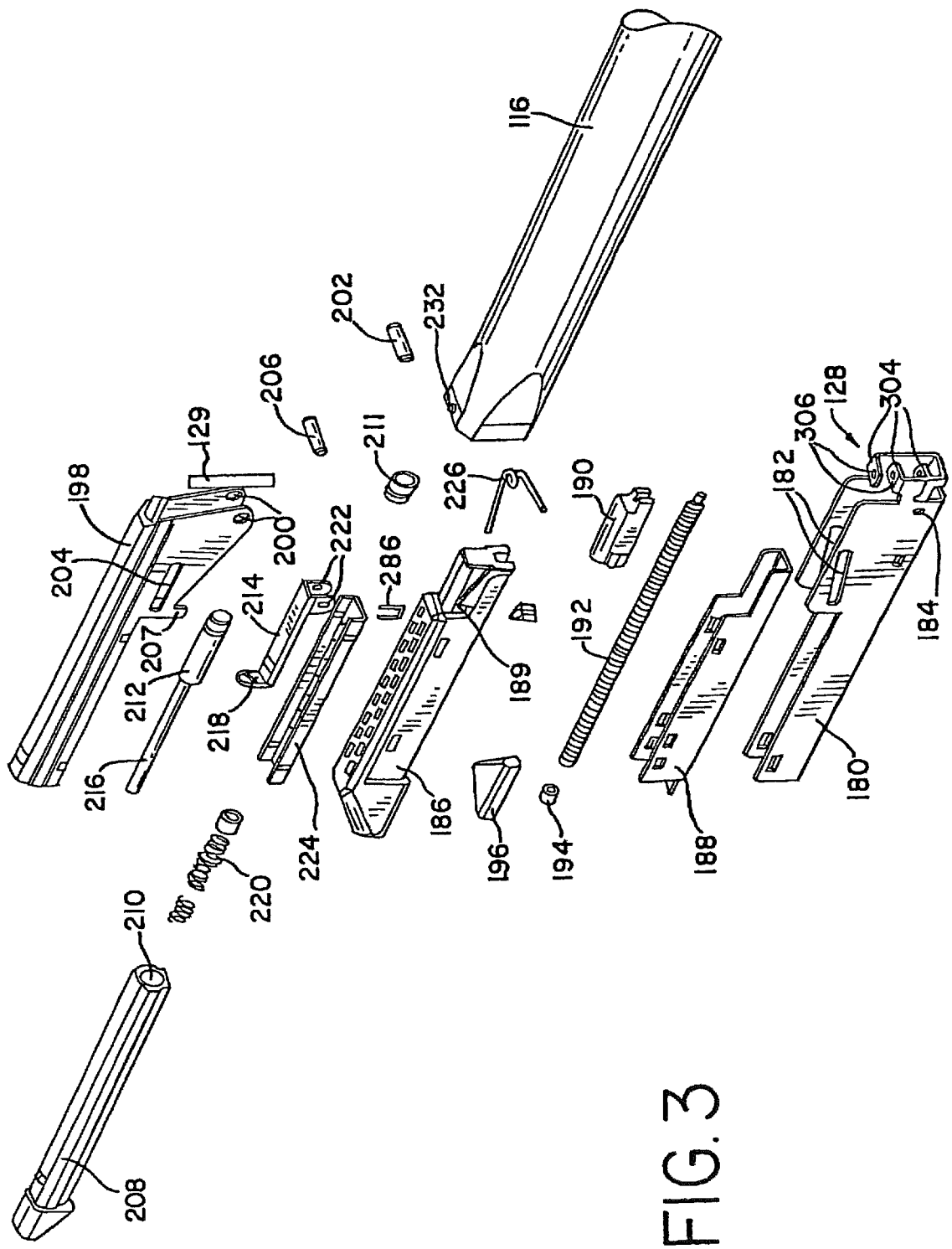
FIG. 3 is an exploded perspective view of the end effector assembly (the clamping and stapling jaws) of the instrument of FIG. 1.

FIG. 1 is an overall cross-sectional view of a surgical stapling instrument, generally at 100, employing the present invention and particularly suited for endoscopic or laproscopic isolation of the left atrial appendage. As shown in FIGS. 1-3, the illustrated instrument 100 includes a proximal handle portion or assembly, generally at 102, a distal end effector or implement portion or assembly 104 and an intermediate barrel or shaft portion or assembly, generally at 106, connecting the handle and the effector portions. In this form, the present invention is particularly well suited for endoscopic application, where the end effector is inserted through a trocar or like device and is operated by the handle portion, which remains outside the patient.

Although the present invention is illustrated in the context of an endoscopic stapler, the present invention is not, in its broader aspects, limited to a stapler or to a particular type of end effector. Accordingly, it should be understood that the following description of the present invention in its present and preferred stapler construction is for the purposes of illustration, and not for the purposes of limiting various aspects of the present invention to the specific structure or form shown in the drawings.

Turning first to a brief overview of the illustrated instrument, as shown in FIG. 2, the handle portion 102 is divided into two halves or shells 108 that, when joined, house or mount the various mechanical and hydraulic parts involved in clamping the effector jaws together and firing the staples. In brief, each handle shell 108 includes a fixed grip area 110, a body portion 112 and a distal spherical portion 114 that cooperates with other parts to provide a swivel or gimbal action between the handle assembly and the barrel assembly 106, as will be described in more detail later. The handle may be made of any suitable material such as rigid, injection molded plastic or the like.

The barrel portion 106 comprises a hollow elongated cylindrical barrel 116 preferably made of suitable metal, although rigid plastic may also be used. The barrel is sufficiently small to allow introduction of the instrument through the lumen of a trocar or other introductory device employed in the surgical procedure for access through the skin of the patient to the surgical site. The barrel 116 contains the fluid flow tubing 118 and 120 of the hydraulic actuation systems for, respectively, closing the distal effector jaws and firing staples. In addition, the barrel contains a balloon retractor subassembly, generally at 122 in FIG. 2, that positively returns an actuator balloon to its retracted position after staple firing, as also will be discussed in more detail later.

The preferred effector or implement end 104 of the instrument may be seen in FIGS. 1 and 3. In the illustrated embodiment, the effector end or implement is in the form of a pair of jaws for clamping and stapling tissue. The effector end includes a lower jaw 124 and an upper jaw 126 pivotally attached to the lower jaw. The lower jaw contains a prefilled staple cartridge that are ejected by hydraulic action. The upper jaw includes the anvil, which includes a series of curved convex surfaces for forming the staple ends over to clench the tissue gripped between the jaws. Of course, the jaw positions may be reversed and other end effector arrangements may be employed without departing from the present invention. For example, the jaws may include multiple rows of staples with a cutting element located between the rows to separate tissue upon stapling. The end effector could also include electrodes for radio frequency sealing, or could comprise scissor blades for cutting tissue. These are just a few of the additional possible applications of the instrument of the present invention.

The end effector assembly of FIGS. 1 and 3 is mounted to the distal end of the barrel 116 at an articulation joint, generally at 126, which allows relative side to side pivoting of the end effector jaws after they protrude through the distal end of the introduction trocar. In the preferred embodiment, the end effector is spring-biased at the articulation joint to extend proximately 30 degrees in the direction out of the plane of the paper in FIG. 1. This feature of the illustrated instrument places the jaws in a preferred position for clamping and sealing the left atrial appendage of a human heart after entry between the ribs, in the procedure described in U.S. Pat. No. 5,306,234 to Dr. Johnson.

The Handle Assembly

Turning now to FIG. 2, as pointed out earlier, the jaw clamping and staple firing of the present invention are hydraulically controlled, and each is controlled by a separate hydraulic system. The handle portion or assembly 102 mounts a hydraulic cylinder block 130 that includes a pair of parallel bores 132 and 134 for receiving, respectively, a piston for jaw clamping 136 and a piston for staple firing 138. The proximal end of each piston includes a gear rack for rack and pinion type cooperation with the gear teeth of separate clamping and for firing members. Coil springs 140 and 142 bias each piston toward a proximal, low pressure position.

It is contemplated that the hydraulic fluid used in these systems will be water or a combination of water-alcohol mixture to prevent the growth of organisms within the hydraulic fluid. Incompressible liquids are the preferred hydraulic fluid, but other liquids, and possibly even gases, could also be used as the hydraulic fluid, if so desired.

The clamping piston is moved forward, in a distal direction, by pivoting of clamp lever 144 toward the fixed pistol grip 110. Clamp lever 144 is pivotally mounted on cylindrical boss 146 that extends from the inside surface of handle shell 108. The clamp lever includes a raised arcuate segment that carries a series of gear teeth 148 on its upper surface, which engage with the teeth of the clamping piston gear rack 136, forming a rack and pinion arrangement. Upon pivoting of the clamping lever rearwardly, the clamping piston is forced forward or distally into bore 132, pressurizing the liquid located within the closed hydraulic system for the clamping action.

Figure 10:
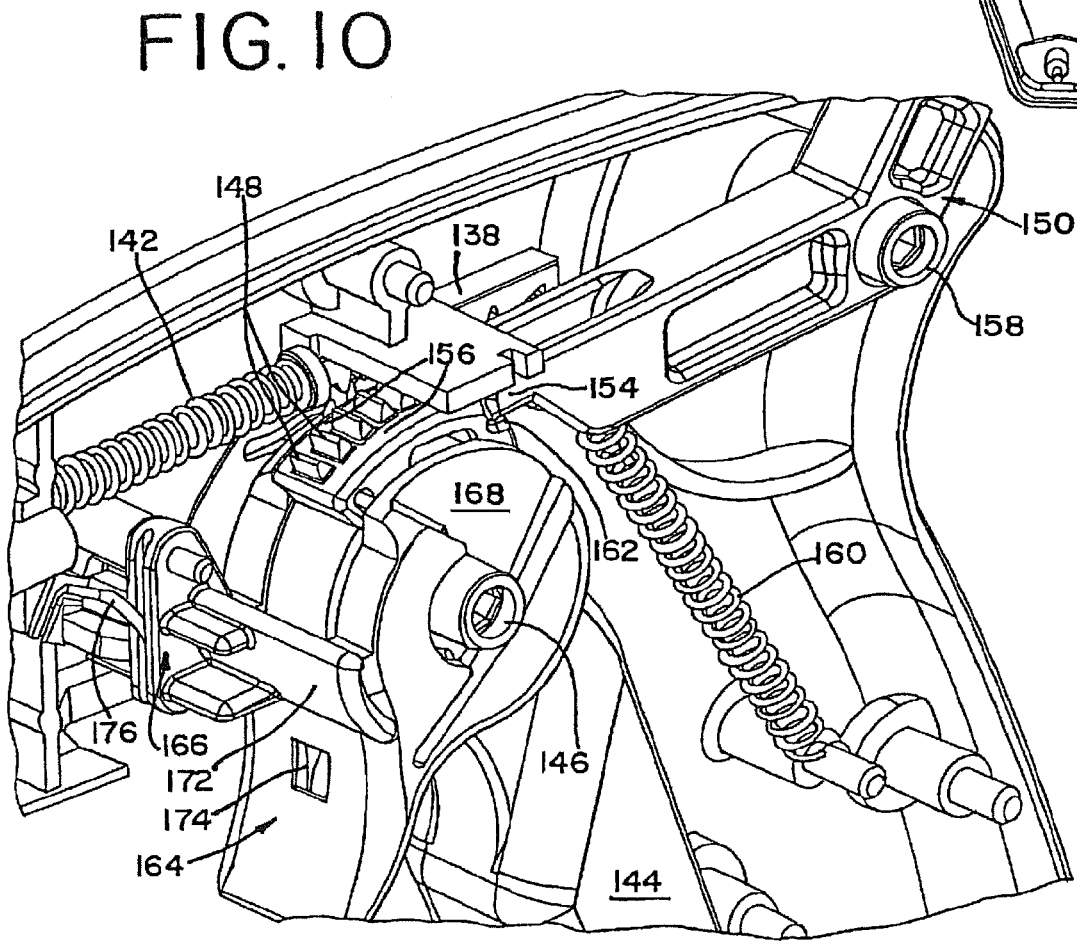
FIG. 10 is an enlarged perspective view of the handle assembly of FIG. 1 in a fully clamped position and with portions removed to better show the relationship between the clamping lever and firing trigger.

To lock the clamp lever in the clamped position, the handle assembly includes a release button 150. The release button has a proximal external thumb release tab 152 and a distal nose 154 that cooperates with upper surfaces 156 of the clamp lever that flank the gear teeth 148. The release button 150 is pivotally mounted on a cylindrical boss 158 (extending from the inside surface of housing shell 108) intermediate the thumb tab and the nose piece so that downward pressure on the thumb tab raises the nose piece. Coil spring 160 is attached to the release button to bias the nose downwardly. As will be described in more detail later, when the clamp lever is pulled to the clamping position, the nose of release button 150 falls into a locking notch 162 in the clamp lever to hold it in the clamped position. After the jaws are clamped, the next action required of the surgeon is to fire the staples so that they extend through and clench the tissue that is gripped between the closed jaws. To carry out this action, the handle assembly includes a firing trigger 164 and a safety latch 166. The firing trigger is also pivotally mounted on boss 146 of the handle. As can be seen in FIGS. 2, 12 and 10, in that order, the firing trigger has a pair of spaced-apart side walls 168. The upper end of the clamping lever is located within the space or slot between the side walls of the firing trigger, and the boss 146 extends through both the firing trigger and clamping lever.

The firing trigger is biased by torsion spring 170 to an extended firing position. However, until firing is needed, the trigger is held in retracted position within the handle by the safety latch 166. The safety latch 166 includes laterally extending wings 172 that extend through access openings or windows 174 in each side of the handle body 112.

The safety latch is also pivotally mounted to the body and biased by a spring wire 176 to a latched position, where it retains the firing trigger in an inaccessible retracted position within the handle until the surgeon wishes to fire the staples. At that time, the firing trigger is deployed by pushing on the end of one of the wings 172 that extends through side window in the handle. This action pivots the safety latch to a release position, allowing the firing trigger to deploy downwardly, due to the bias of torsion spring 170. The surgeon may then squeeze the firing trigger, causing gear teeth 258 on the upper surface of the firing trigger to move the staple firing piston forward, pressurizing the hydraulic fluid within the staple firing hydraulic circuit. The details of the various clamping and staple firing actions is shown more clearly in later drawings, where extraneous parts or pieces have been removed to clarify an understanding of the different operations of the illustrated device.

The Effector Assembly

Turning now to the distal or effector end of the instrument 100, the parts of the distal end may first be seen in FIG. 3, an exploded view.

The lower jaw 124 includes a bent u-shaped sheet metal channel 180 that includes an inclined slot 182 in each side wall and a pivot opening 184 in each side wall, where the upper jaw is pivotally attached to the lower jaw. The proximal end of the channel 180 is also formed into an articulation joint or knuckle, generally at 128, for pivotally joining, via pivot pin 129, with the distal end of the barrel or shaft 116.

The lower jaw includes a replaceable staple supply cartridge, generally at 186, which fits into a u-shaped bent metal receiver 188 located within channel 180. The staple cartridge includes a side recess 189 for receiving a locator tab on the upper jaw where the jaws are clamped together. The lower jaw also includes a balloon housing 190 for housing the staple actuation balloon 192. The balloon terminates in a rounded balloon tip 194 for engaging against a wedge 196 in the staple cartridge. Axial expansion of the balloon forces the wedge through the staple cartridge, the sloped forward surface of wedge 196 forcing the staples upwardly out of the cartridge.

The upper jaw 126 of the end effector includes an anvil body 198 that has pivot openings 200 for pivotal attachment to the lower jaw pivot openings 184 by pivot pin 202. The anvil body 198 also includes a pair of slots 204 that cooperate with inclined slots 182 in the lower jaw, via slide pin 206, for relative opening and closing of the jaws. The anvil body further includes a staple cartridge locator tab 207, for insertion into the side recess 189 of the staple cartridge for positively locating the staple cartridge when the jaws close.

The upper jaw 126 also includes a nose piece 208 that has a central bore 210 for receiving piston 212. The piston 212 cooperates with a linkage 214 to open and close the jaws. More specifically, piston rod 216 extends through linkage eye 218 and through a coil spring 220 and into the nose piece bore 210 (with bushing 211 closing the proximal end of the nose piece bore except for a small hydraulic fluid port in the bushing). The linkage 214 includes pivot openings 222 that cooperate, via slide pin 206, with the slots 204 in the anvil body and inclined slots 182 in the lower jaw channel, as will be described in more detail later. Finally, the upper jaw includes an anvil former 224 which has concave pockets for receiving and bending over the staples to clench tissue gripped between the jaws, and a torsion spring 226 for laterally biasing the jaws to a angle position relative to the barrel 116.

The Barrel Assembly

Referring to FIG. 2, the barrel or shaft assembly 106 includes the barrel or shaft 116 which houses the hydraulic tubing 118 and 120 for the closing and firing systems and the balloon retractor subassembly 122. As mentioned earlier, the barrel or shaft 116 is a hollow, cylindrical, elongated tube, and is preferably made of metal, although suitably strong plastic may also be used. The proximal end of the barrel 116 includes opposed slots 228 for attachment to swivel joint 298 between the handle and barrel. The distal end of the barrel has upper and lower pivot openings 232 for receiving pivot pin 129 that joins the barrel and jaws to form the articulation joint 128.

The balloon retraction subassembly 122 located within the barrel includes a balloon retractor tube 234 extending longitudinally within the barrel and closed at each end by a bushing 236. Hydraulic fluid from the staple firing piston communicates with the interior of the balloon retractor tube through tubing 120 that is attached to a hydraulic fluid port in the proximal bushing 236. The hydraulic fluid path extends through the distal end bushing 236 to an extension of tubing 120 that continues to the proximal end of balloon 192, located in the lower jaw of the effector assembly.

The balloon retractor tube 234 encloses, as best seen in FIGS. 26-28, a cable cap 238 attached to the proximal end of a retractor wire 240. Retractor wire 240 extends through the distal bushing 236, through the extension of tubing 120 and through the balloon to the balloon tip 194. Coil spring 242 extending between the distal bushing of the retractor tube and the cable cap 238 biases the end cap to a proximal position, which corresponds to a balloon retracted position. With this arrangement, expansion of the balloon pulls, via wire 240, cable cap 238 in a distal direction, compressing coil spring 242. When the hydraulic force is reduced after staple firing, the force of the compressed coil spring pushes the cable cap rearwardly (proximally), pulling the wire 240 and thus the balloon to a retracted or deflated position.

The Clamping Action

FIGS. 4-9 show cross-sectional views of the handle portion and end effector portion with respect to the clamping operation, with parts and pieces relating to the firing action removed for better understanding of the clamping action.

Figure 4:
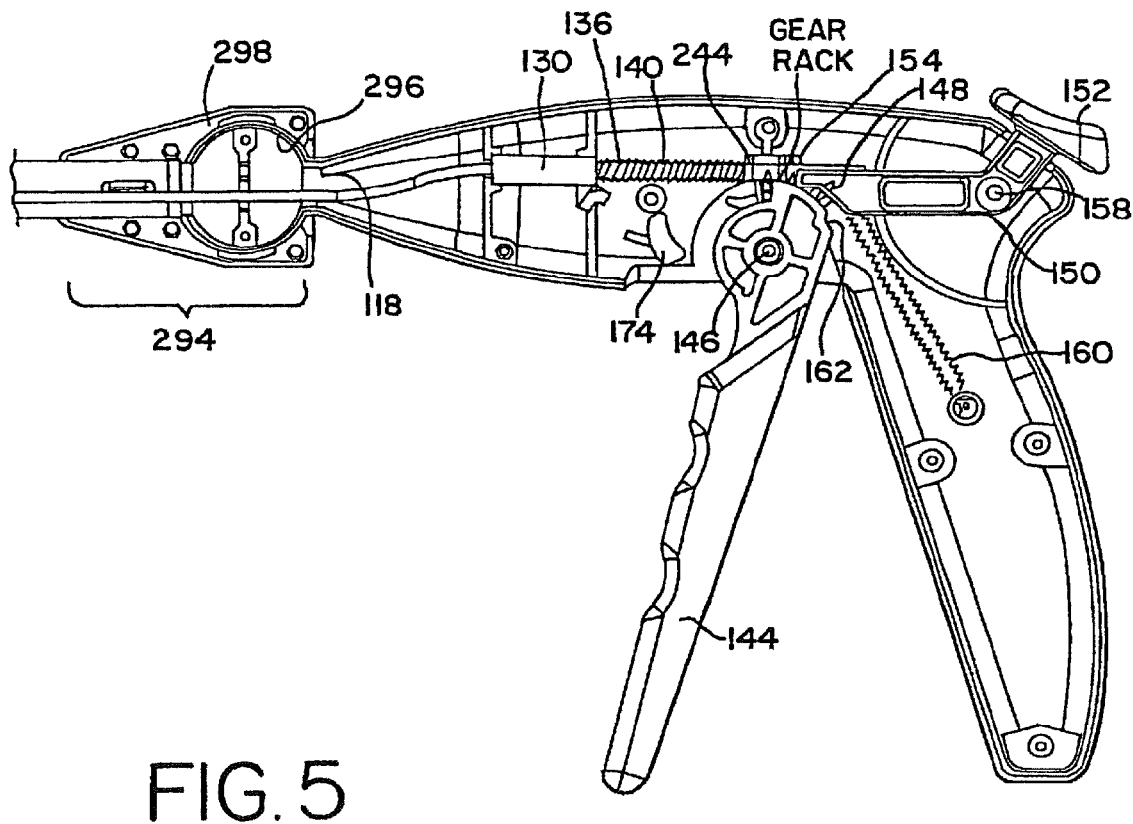
FIG. 4 is a vertical cross-sectional view of the handle assembly and articulation joint between the handle and barrel of the instrument of FIG. 1, with the jaws in the fully open position, and with portions pertaining to the staple operation removed for better illustration of the clamping operation.
Figure 5:
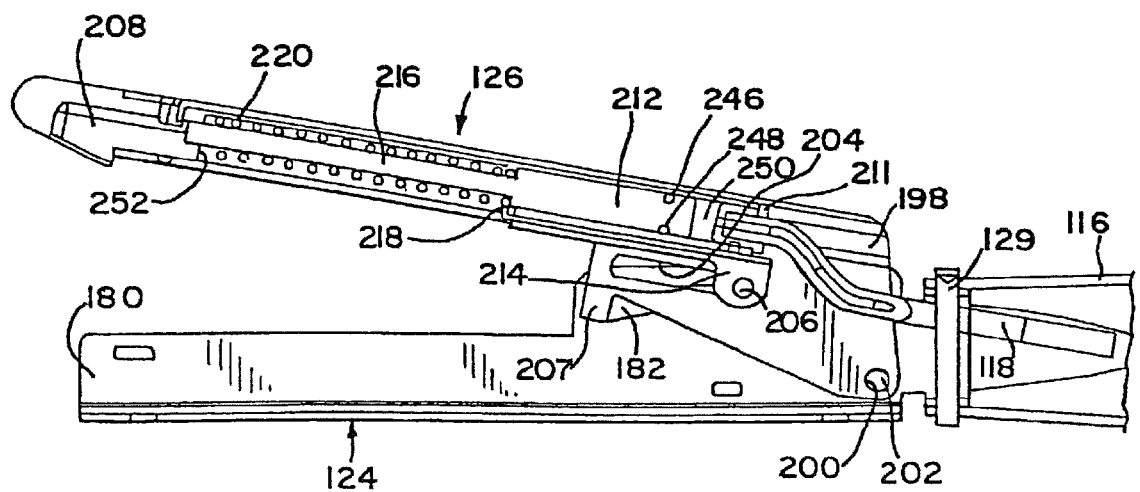
FIG. 5 is an enlarged vertical cross-sectional view of the end effector portion of the instrument of FIG. 4, with the jaws fully open, and with portions relating to stapling removed for better understanding of the clamping operation.

FIGS. 4-5 show the handle assembly and effector assembly as they are in the jaws open position. Turning to FIG. 4, the handle assembly 102 is shown there in cross-sectional view, illustrating the clamp lever 144 pivotally mounted on boss 146, the hydraulic cylinder block 130, and the clamping piston 136 which includes a gear rack at its proximal end. Flexible tubing 118, which may be plastic, silicone or other suitable material, extends from the clamping piston bore 132 to the distal end jaws for effecting the clamping action. The tubing is flexible at least in the vicinity of or in proximity to the articulation joints so as not to substantially interfere with or impair articulation of the joint. Compressed coil spring 140 extends between the hydraulic cylinder block 130 and flange 244 located on the piston. Coil spring 140 biases piston toward a proximal, low pressure position, so as to bias the effector jaws in an open position.

In the position illustrated in FIGS. 4-5, the jaws are fully open, the clamp lever 144 is fully extended, and the clamping actuation piston is in the position fully to the right in the non-pressurized proximal position. The distal nose 154 of the release button 150 rests on the smooth upper surfaces 156 of the clamp lever 144 (See FIG. 10). Coil spring 160 is in tension, pulling the nose of the release button downwardly. As better seen in FIGS. 1 and 10, the distal or nose end of the release button is slotted. The clamping piston gear rack is slidably received within the nose piece slot, and the nose piece therefore prevents lateral, side-to-side shifting of the piston gear rack.

Turning to FIG. 5, showing the end effector jaws in the open position, comparable to FIG. 4, the effector jaws are shown in cross-sectional view, without a staple cartridge, to better illustrate the clamping function. As shown there, the anvil body 198 is pivotally mounted by pivot pin 202, which extends through pivot openings 184 of the lower jaw channel and 200 in the upper jaw anvil body. Slide pin 206 extends through slots 182 in the lower jaw channel, slots 204 in the upper jaw anvil body, and through pivot openings 222 of the linkage 214. Piston 212 is located within the bore 210 of the nose piece 208. The piston includes an o-ring 246 located in an o-ring slot 248 around the circumference of the piston to seal against the leakage of hydraulic fluid.

The proximal end of the nose piece is closed by a bushing 211, to which the hydraulic tubing 118 is attached. The fluid space 250 located between bushing 211 and piston 212, in normal operation, will be filled with hydraulic fluid. Upon pressurization of the hydraulic fluid, the piston will be moved distally or forwardly (to the left in FIG. 5). As will be recalled, the piston rod 216 extends through the eye 218 of the linkage 214, and movement of the piston to the left also pushes the linkage to the left.

The forward or distal end of the nose piece is slotted on the underside to receive the eye 218 of linkage 214. As the piston moves to the left, action of the slide pin 206 moving along slots 204 in the upper jaw anvil body and 182 in the lower jaw channel pull the slots together, closing the jaws. Movement of the piston also compresses the coil spring 220 that extends between an inner shoulder 252 on the nose piece and the linkage eye 218. Accordingly, in the event of failure of the hydraulic clamping system, the spring 220 will move the piston 212 to a jaw-open position.

Figure 6:
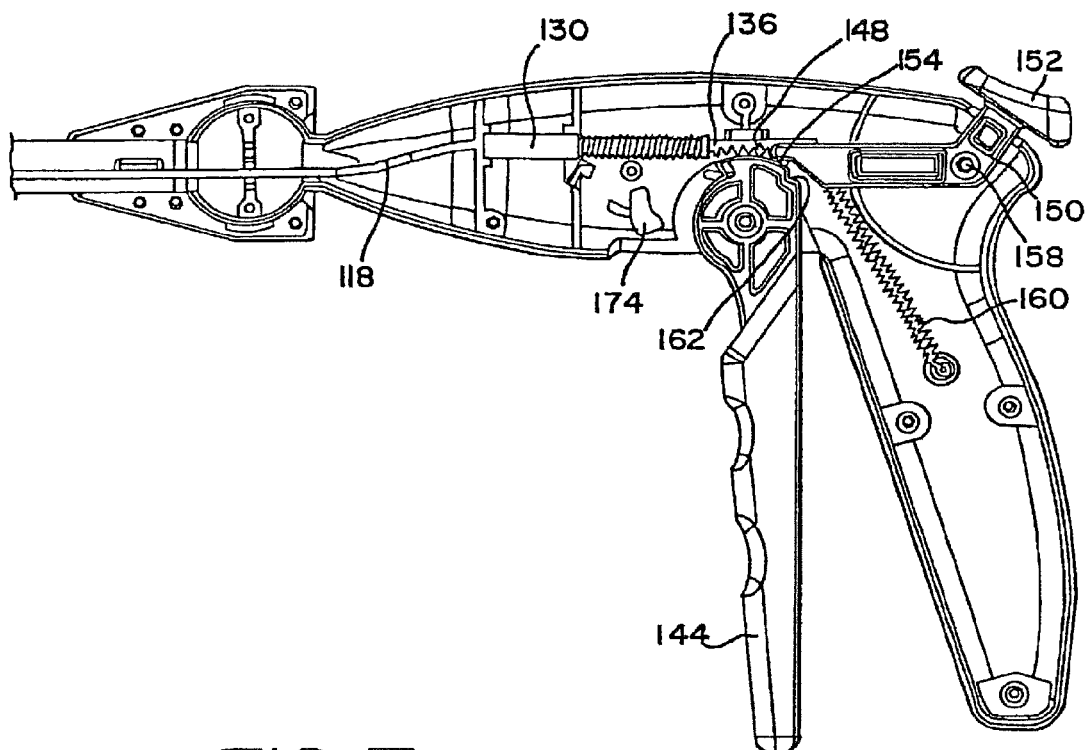
FIG. 6 is a vertical cross-sectional view of the handle assembly of FIG. 4, but with the jaws at an intermediate position.
Figure 7:
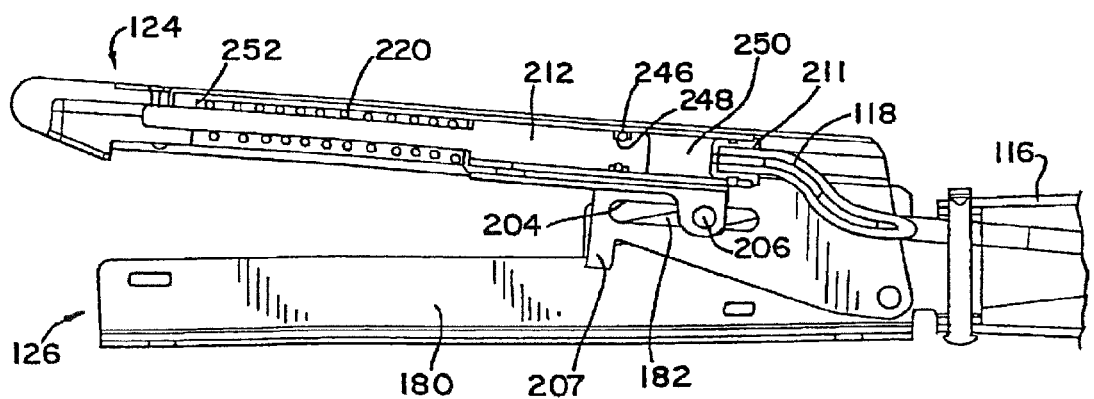
FIG. 7 is an enlarged vertical cross-sectional view of the end effector portion of FIG. 5, but with the jaws at an intermediate position.

FIGS. 6 and 7 show the handle assembly 102 and end effector assembly 104 in the position where the jaws are partially closed. As can be seen in FIG. 6, the clamp lever 144 has moved partially toward the fixed pistol grip 110. The rack and pinion gear arrangement between the clamping piston 136 and clamp lever gear teeth 148 has moved the clamping piston slightly distally or to the left in FIG. 6, pressurizing the hydraulic fluid within the bore 132 of the hydraulic cylinder block 130. Inasmuch as this is a closed hydraulic system full of normally incompressible liquid, little movement is required to generate very high pressures within the hydraulic system. This increased pressure is transmitted through the tubing 118 to the piston 212 located in the upper jaw at the distal end of the instrument.

Turning to FIG. 7, increased hydraulic pressure through the tubing 118 and bushing 211 has moved the piston 212 slightly in the distal direction (to the left in the drawing) pulling the linkage 214 in a distal direction, and moving slide pin 206 distally along slots 204 in the upper jaw anvil body and 182 in the lower jaw channel. This action of the linkage and pin has drawn the upper and lower jaws of the distal end together.

Figure 8:
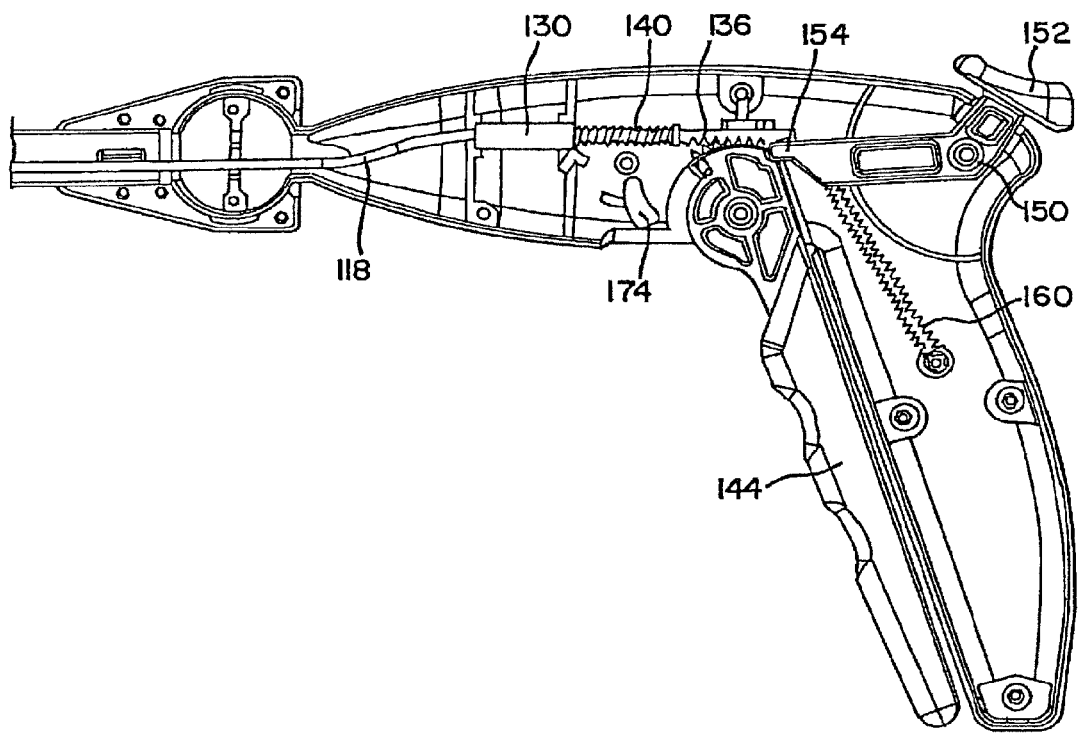
FIG. 8 is a vertical cross-sectional view of the handle assembly of FIG. 4, but with the jaws at a fully closed position.
Figure 9:
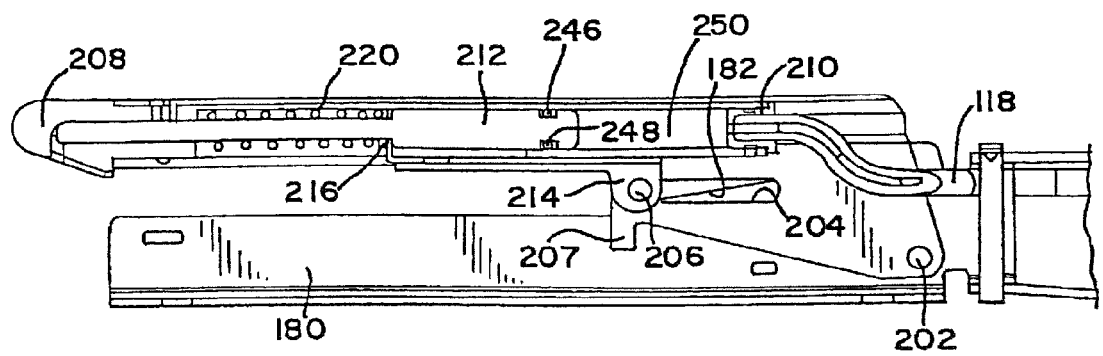
FIG. 9 is an enlarged vertical cross-sectional view of the end effector portion of the instrument of FIG. 5, but with the jaws at a fully closed position.

FIGS. 8 and 9 show the instrument 100 with the jaws 124 and 126 fully closed or clamped. As seen in FIG. 8, the clamp lever 144 has now been pivoted fully against the pistol grip 110. Nose end 154 of the release button 150 has dropped into the locking notch 162 in the upper area of the clamp lever, preventing the clamp lever from rotating clockwise, unless the thumb release tab 152 is depressed. Coil spring 160, which is in tension, holds the release button in this locked position.

In the fully clamped position, the gear teeth 140 on the upper end of the clamp lever 144 have advanced the clamping piston 136 more completely in the compressed direction (to the left in the drawing), creating increased pressure in the clamping hydraulic circuit and further compressing piston coil spring 140.

As shown in FIG. 9, the increased pressure of the hydraulic liquid, communicated through the tubing 118 and into the bore of the nose piece 208 has moved the piston 212 in upper jaw 126 distally. As a result, the piston 212 has pushed the linkage 214 toward the distal end of the jaw and the slide pin 206 to the distal end of the slots 204 in the upper jaw anvil body and 182 in the lower jaw channel. This action brings the jaws to the fully closed or clamping position. Again, coil spring 220 is compressed, biasing the piston to the low pressure or jaws open position.

When it is desired to open the jaws; the above described action is reversed. The thumb tab 152 on the release button 150 is depressed, raising the nose 154 of the release button from the lock-out notch 162 in the clamp lever, and allowing the clamp lever to rotate clockwise to the open position. The bias of the compressed springs 220 in the upper jaw and 140 in the handle force the clamping piston 136 outwardly of the bore 130 in the hydraulic cylinder block to a low pressure position, where it was initially, as seen in FIG. 4 for example, and the jaws open by the reverse movement of slide pin 206 in the slots 204 in the upper jaw anvil and 182 in the lower jaw channel.

The Stapling Action

Turning now to the stapling action, the hydraulic circuit of the stapling action may be seen in FIGS. 12-26. As was pointed out earlier, the hydraulic system for the firing circuit has, at the proximal end, the staple firing piston 138, which is slidably received within bore 134 of the hydraulic cylinder block 130. As with the clamping hydraulic circuit, the firing hydraulic circuit is a closed circuit, pre-filled with essentially non-compressible liquid, although other fluid and even compressible gas may be employed if desired. Hydraulic fluid is conducted through flexible tubing 120, balloon retractor tube 234, tubing 120 extension and into the balloon 192, so that the tubing is located in proximity to the joints to allow articulation without substantial interference and without complicated mechanical structures for transmitting control actions to the end effector. Both clamping and firing pistons include one or more o-rings to seal against the respective bore to prevent leakage of hydraulic fluid.

Figure 11:
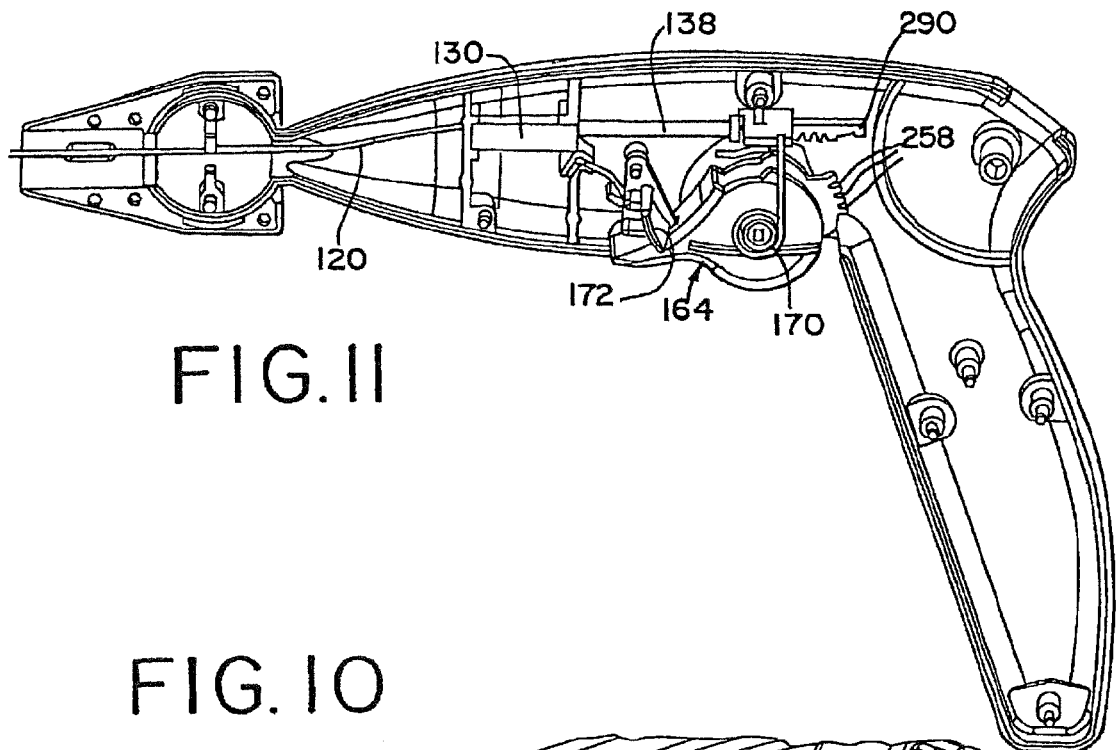
FIG. 11 is a perspective view of the handle of the instrument of FIG. 1, with portions removed to better illustrate the firing trigger and safety latch, and with the firing trigger in the undeployed position.
Figure 14:
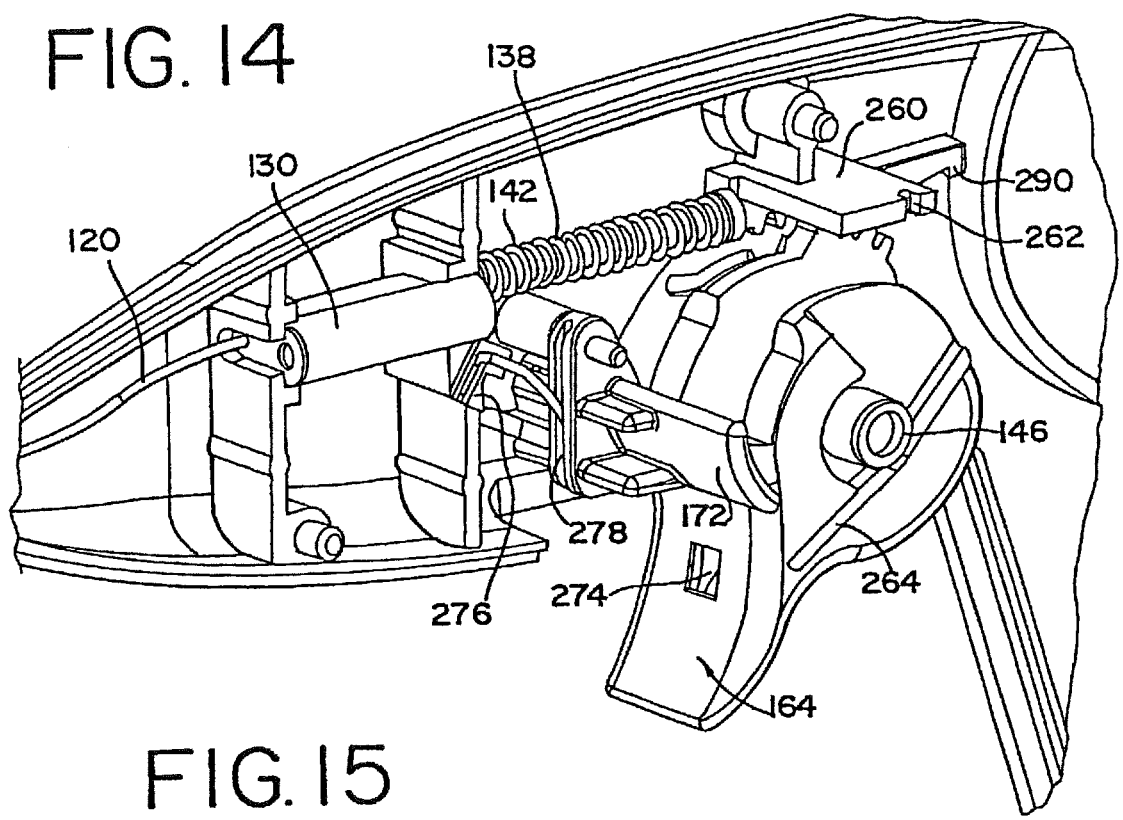
FIG. 14 is a perspective view of the handle of FIG. 11, taken from a different angle to better illustrate various aspects of the firing trigger and safety latch.
Figure 15:
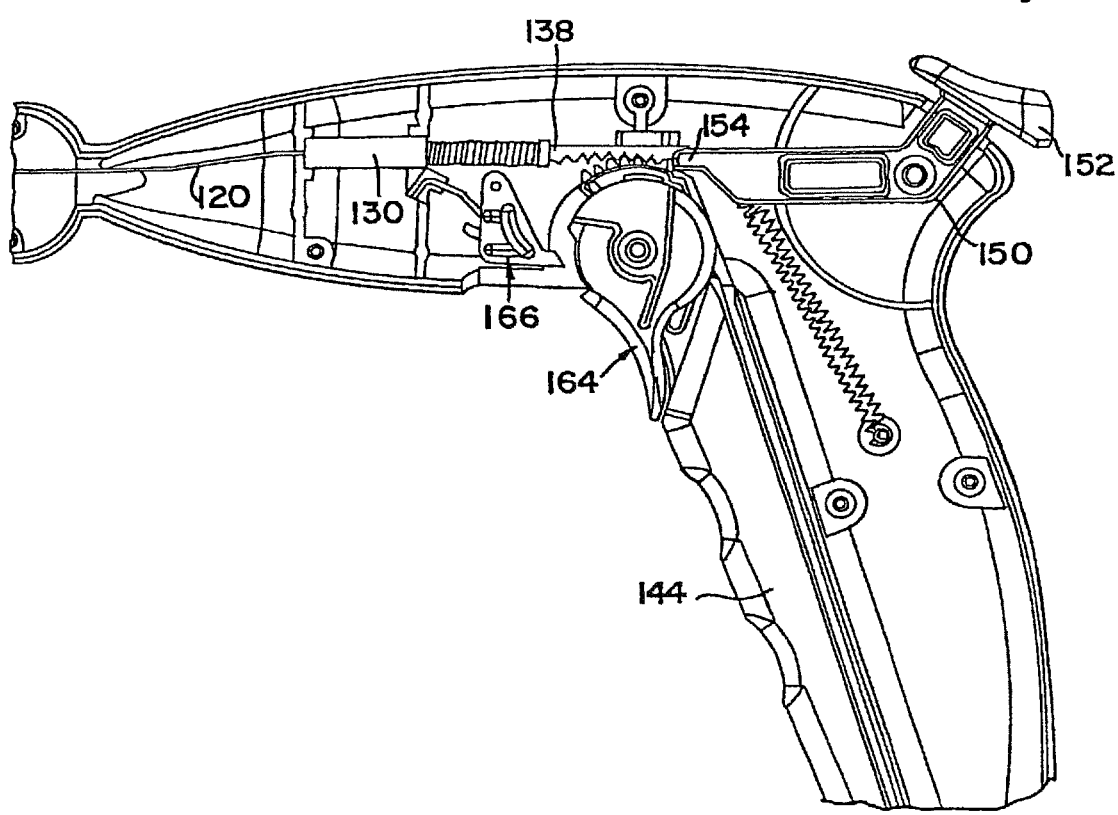
FIG. 15 is a side view of the handle of the instrument of FIG. 1, with parts removed to illustrate the firing trigger and safety latch, with the firing trigger in the fired position.

The handle mechanism by which the staple firing sequence occurs is perhaps best seen in FIGS. 11-15, which are views of the inside of the handle, with parts relating to the clamping action removed. Turning first to FIG. 11, the firing trigger 164 is shown in the retracted and undeployed position, where it is held by the safety latch 166 until the surgeon takes the positive step, after being satisfied with the clamping, to deploy the firing trigger. As may be seen in FIG. 12, the firing trigger is pivotally mounted on the same boss 146 as the clamp lever 144. More specifically, the firing trigger includes a pair of spaced apart circular side or end walls 168, one of which includes gear teeth 258 for cooperation with the gear rack of the staple-firing piston 138, and the other of which mounts the torsion spring 170, which biases the trigger to the deployed position. In the completed assembly (See FIG. 10), the upper end of the clamp lever 144 is located and captured between the spaced-apart circular walls 168 of the firing trigger, rotating freely relative to the firing trigger on the boss 146. As shown in FIG. 14, the rack of the staple firing piston is constrained against upward movement by a horizontal plate 260. The horizontal plate also includes an aperture 262 for receiving one arm of the torsion spring 170. The other arm of the torsion spring is captured in a slot 264 provided in the side face of the firing trigger.

To hold the firing trigger in a retracted and inaccessible position until after the surgeon is satisfied with the clamping, the present invention employs the safety latch 166. As seen in FIGS. 1 and 12, the safety latch 166 includes a vertical wall or body 266 which mounts, at its upper end, opposed pivots 268 that extend into hollow bosses 270 of the handle, allowing the safety latch to pivot or swing about those pivot points. As seen in FIG. 13, a tongue or tab 272 protrudes proximally from the face of the safety latch for engagement with a window 274 (as best seen in FIG. 14) in the safety latch trigger. One end of spring wire 176 is attached, as seen in FIG. 14, to partition 276 of the handle. The other end of the spring wire is located in a slot 278 in the back side of the safety latch body 266. Thus, the spring wire biases the safety latch counterclockwise, so that the tongue 272 enters the trigger window 274 when the trigger is moved to a retracted position.

As described briefly earlier, the safety latch includes a pair of wings 172 extending laterally from the body 266, and through windows 174 in the side walls of the handle. When the surgeon is satisfied with the clamping action, he or she may, by pushing on the end of the wings protruding through the window, pivot the safety latch clockwise to remove the latch tongue 272 from the firing trigger window 274, and allow the firing trigger to deploy under the biasing force of the torsion spring 170.

In the deployed position, the firing trigger is accessible to the surgeon for executing the firing action of the staples. Similar to the clamping action, pulling on the trigger causes, through the meshing of gear teeth 258 and the teeth of the staple firing piston rack, the staple firing piston to move distally to compress the hydraulic fluid in the firing piston bore 134 and to compress the coil spring 142 that surrounds the firing piston. As hydraulic pressure is increased by the movement of the piston in the handle, the increased pressure is transmitted to the balloon 192 through the hollow tube 120, the balloon retractor tube 234, and tubing extension.

The staple firing sequence in the distal lower jaw is most easily understood by reference to FIGS. 18-25. FIG. 18 is a perspective view of the end effector, which shows both the top and bottom jaws 124 and 126 of the preferred embodiment of the present invention. In FIG. 19, the upper jaw is removed, and only the lower jaw with the staple cartridge 186 remains. In that figure, the inclined slots 182 in the channel 180 are readily visible, as is the pivot opening 184 by which the upper jaw is pivotally attached to the lower jaw. The articulation joint 128 and pivot pin 129 mounting the end effector to the distal end of the barrel are also visible in FIG. 19.

In FIG. 20, the channel is removed, and we can now see the receiver 188, containing the staple cartridge 186, and also the balloon housing 190. A balloon housing tab 280 is located on each side of the balloon housing 190 for snap interfit in side apertures 284 in channel 180 (see FIG. 19).

FIG. 21 shows the distal end of the lower jaw with the receiver and staple cartridge, in large part, removed. In this figure, tubing 120, which conveys the hydraulic fluid to the balloon, is shown entering the rear or proximal end of the balloon housing 190. The rear of the balloon housing also includes an arcuate or cutout area for accommodating the pivot pin 202 that pivotally mounts the lower and upper jaws together.

The balloon housing 190 has a generally U-shaped cross-sectional shape, forming a channel for receiving the deflated or retracted balloon. The convex, hemispherically shaped tip 194 of the balloon may be seen at the distal end of the housing in FIG. 21. FIG. 21 also shows the cam or wedge 196 which, when forced axially through the staple cartridge, ejects the staples. The proximal end of the wedge is generally spherically concave in shape to receive the spherically convex tip of the balloon. The wedge also includes a ramp or cam surface 284.

Within the staple cartridge, as is well known in the prior art, each staple 286 is located atop a driver 288, and the drivers are aligned in a generally axial direction. As the wedge is forced forward or distally through the cartridge, the drivers are forced up the ramp surface of the wedge, ejecting the staples and forcing them against the anvil former that is located in the upper jaw.

The balloon 192 has a fluted wall which allows it to be repeatedly expanded and retracted. As shown in FIG. 22, the balloon is in the retracted position. When the firing trigger is pulled, and the staple firing piston increases hydraulic pressure in the firing circuit, the balloon expands axially, as shown in FIG. 23, forcing the wedge through the cartridge and firing the staples into and through the tissue and forming the ends of the staples over to clench the tissue gripped there between.

FIGS. 37 and 38 shows a vertical side cross-sectional view of the balloon when expanded and retracted, and showing the fluted or folded accordion configuration of the balloon.

Figure 16:
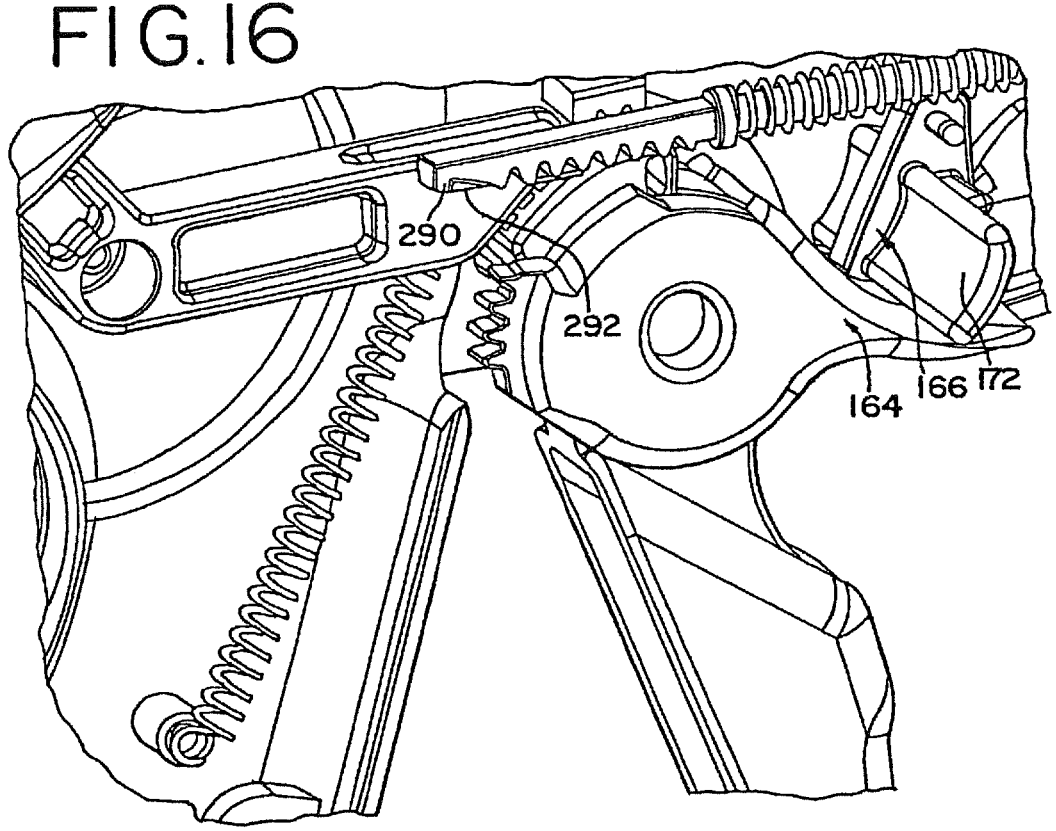
FIG. 16 is an enlarged perspective view of a portion of the handle assembly of the instrument of FIG. 1, taken from the back side of the instrument as depicted in FIG. 1 and illustrating, among other things, a firing lockout feature that prevents staple firing until the instrument is fully clamped.
Figure 17:
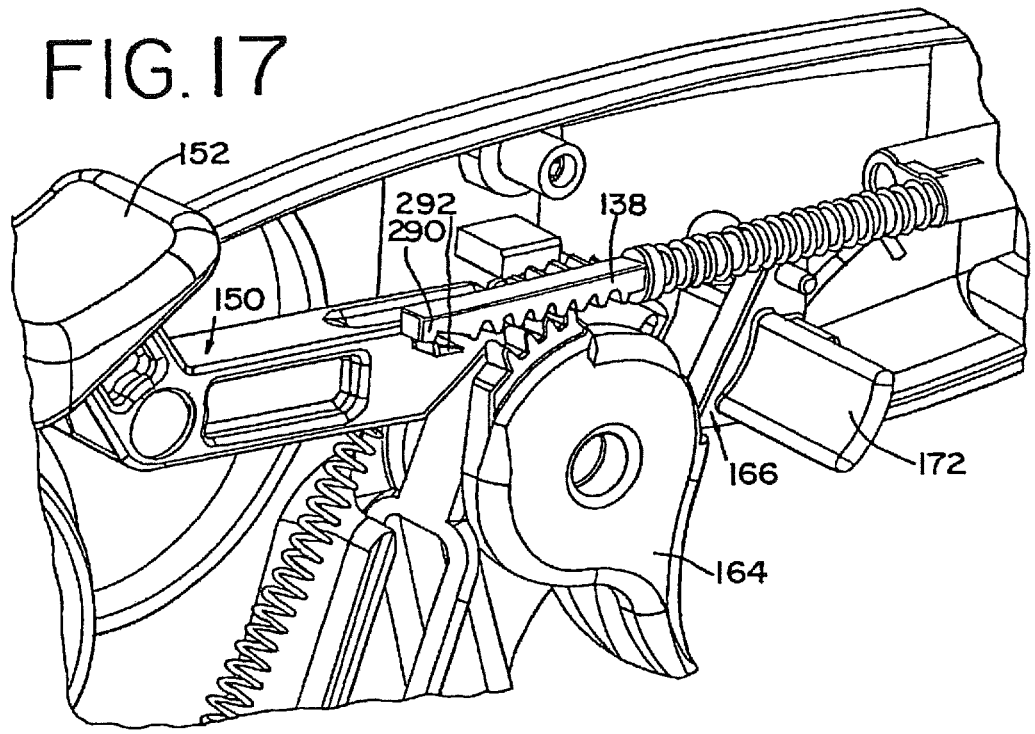
FIG. 17 is a view comparable to FIG. 16, but showing the trigger lockout in a released position.

There is yet one additional safety feature associated with the firing of the staples in the instrument 100. Turning to FIG. 16, a depending hook 290 is located at the proximal end of the staple firing piston 138. That hook is engaged by a raised tab 292 on the nose 154 of the release button 150 until the jaws are clamped. This interference prevents axial movement of the staple firing piston until after the jaws have been fully clamped. It may be recalled from FIG. 8, that after the clamping lever is fully retracted, the nose of the release button falls into the locking notch 162 in the upper surface of the clamp lever 144. When that occurs, the raised tab on the release button drops out of engagement with the staple firing piston (see FIG. 17), allowing the piston to be moved by the firing trigger. Until such time, however, as the release button drops into the notch in the clamp lever, which occurs only in the fully clamped position, inadvertent or accidental firing of the staples is prevented.

Articulation Joints

It was previously noted that the present invention employs, as illustrated, a swivel or gimbal between the handle portion and the barrel or shaft portion. In the illustrated embodiment, as best seen in FIG. 4, this swivel or gimbal is in the nature of a ball and socket joint 294. As can be seen in FIG. 2, the distal end of each half of the handle includes a hemispherical portion 114, such that when the two handle halves are joined, a ball 296 is formed at the distal end of the handle portion.

Slidably mounted over the ball is a socket 298, also formed by joining two halves, which includes a distal bore 300 for fixedly receiving the proximal end of the barrel or shaft 116. The proximal inside surface of the socket is curved to match the hemispherical shape of the ball, forming a relatively tight but still slidable frictional fit between the ball and socket. For locking engagement of the proximal end of the shaft into the socket, each socket half includes a inwardly extending tab 302, which enters a mating slot 228 in the proximal end of the barrel. This serves to lock the barrel or shaft in a fixed position relative to the socket. Accordingly, with this construction, the handle may be pivoted relative to the barrel or shaft in any direction for up to about 20 degrees.

As clear from the description, the end effector of the present invention is also articulated relative to the barrel or shaft. As best seen in FIGS. 3 and 19, the proximal end of the lower jaw channel 180 is bent into a series of tabs 304, each of which includes a pivot opening 306 in axial alignment with the others. The distal end of the barrel, as also seen in FIG. 3, includes upper and lower axially aligned pivot openings 232. Pivot pin 129 extends through aligned pivot openings 232 in the distal end of the barrel and the aligned pivot openings 306 in the bent tabs of the lower jaw channel 180. This forms a hinged type of joint, allowing pivoting movement of the jaws laterally left and right relative to the barrel.

For particular application of this device to the isolation of the atrial appendage, torsion spring 226 is located on the vertical pin, biasing the jaws at a lateral angle of about 30 degrees relative to the barrel, although other degrees of biasing may be employed, if desired. The spring allows the jaws and barrel to be in alignment as they pass through the trocar in the patient and to the treatment site, but as the distal end of the instrument emerges from the trocar, the jaws move to the angled position to which it is predisposed by the torsion spring.

The end effector may also be mounted for articulation in other directions, such as vertically or at another angle. Also, the articulation joint between the barrel and end effector may be a gimbal or ball and socket type joint, such as used between the barrel and handle, for 360° of articulation. With such a joint, control wires extending from the handle, through the barrel and to the end effector could be used to control the direction and amount of articulation of the end effector to effect precise changes or adjustments to the position of the end effector, as may be required for particularly delicate medical procedures.

FIGS. 39a-e show an alternative embodiment of the present invention. As with the instrument described above, the version shown in FIGS. 39a-e includes a handle portion 102, end effector portion 104 and barrel portion 106. In this embodiment jaws 300 and 302 are pivotally attached at 304 for opening and closing in a scissor-like movement. In addition, each jaw has a terminal portion that is separately pivotable at 308 to allow pivoting of the terminal portion of the jaws at up to a right angle with respect to the barrel portion 106 (as shown in FIG. 39a). With this construction, the jaws may be in general alignment with the barrel for passage through a trocar, and then pivoted to any desired position at the surgical site.

As can be seen from the above description, the present invention has several different aspects and features, which are not limited to the specific device shown in the attached drawings or to the specific procedure for which it is intended. Various of these features may be embodied in other devices for carrying out other procedures, including but not limited to stapling, cutting, grasping, coagulating or other surgical procedures.

Although shown in a manual form, for direct control by the surgeon, the present invention is also applicable in robotically controlled procedures. The hydraulic actuation of the present invention particularly lends itself to small diameter instruments, multi-axis articulation and large force (e.g., clamping or cutting force) generation, which are not only advantageous in manual applications but are also particularly useful in robotic applications, where the instrument operation is remotely controlled through a robotic controller module or unit.

In a robotic application, for example, the end effector assembly could be attached, by way of an elongated shaft, with a remote hydraulic pressure source. The hydraulic pressure source (which may include multiple independent hydraulic pressure sources) could be remotely controlled via electronic or electro-mechanical controller operated by programmable microprocessor alone or in combination with manual control or voice control commands or both, as already known in the art of remote robotic control.

The invention claimed is:

1. A robotically controlled hydraulic end effector system comprising:
   a hydraulically actuated end effector operable in response to hydraulic pressure to effect a first selected action generating a first force;
   an elongated shaft including a proximal end and a distal end, the end effector being carried at the distal end;
   at least one hydraulic pressure source and a hydraulic pressure path between the end effector and pressure source, the hydraulic pressure path transmitting pressure to the end effector and allowing sensing of the hydraulic pressure in the hydraulic pressure path; and
   a controller operatively associated with the at least one hydraulic pressure source for controlling the pressure generated by first selected action in response to user commands.

2. The system of claim 1 wherein the at least one hydraulic pressure source comprises a plurality of pressure sources.

3. The system of claim 1 wherein the first selected action is a clamping action and the first force is a clamping force.

4. The system of claim 1 wherein the controller is responsive to remote user commands.

5. The system of claim 1 wherein the hydraulic pressure source comprises a remote hydraulic pressure source.

6. The system of claim 1 wherein the controller is responsive to manual control commands or voice control commands or both.

7. The system of claim 1 wherein the at least one hydraulic pressure source is controlled remotely by a remote robotic controller in response to manual control commands and/or voice control commands.

8. A robotically controlled hydraulic end effector system comprising:
   a hydraulically actuated end effector operable in response to hydraulic pressure to effect a first clamping action generating a first clamping force;
   an elongated shaft including a proximal end and a distal end, the end effector being carried at the distal end;
   the elongated shaft including an articulation joint allowing articulation in at least one direction;
   a first hydraulic pressure pathway extending through the elongated shaft and communicating between the at least one hydraulic pressure source and the end effector;
   a robotic controller operatively associated with the at least one hydraulic pressure source for controlling the hydraulic pressure in the first pathway in response to remote user commands to control the first clamping action and first clamping force.

9. The system of claim 8 in which the at least one hydraulic pressure source comprises a plurality of pressure sources.

10. The system of claim 8 wherein the at least one hydraulic pressure source comprises a remote hydraulic pressure source.

11. The system of claim 8 in which the end effector includes a first actuator to effect the first action and a second actuator to effect a second action and a second hydraulic pressure pathway and the first and second hydraulic pressure pathways communicate, respectively, with the first and second actuators.

12. The system of claim 11 in which at least one of the actuators includes an expandable member to effect the action.

13. The system of claim 8 in which the controller is responsive to manual control or voice control commands or both.

14. The system of claim 8 in which the hydraulic pressure pathway comprises flexible tubing.

15. A robotic hydraulically actuated tissue stapler system comprising:
   a hydraulically actuated end effector operable in response to hydraulic pressure to effect a first clamping action and to effect a second stapling action;
   a least one hydraulic pressure source in pressure communication with the end effector;
   a robotic controller operatively associated with the at least one hydraulic pressure source for controlling the pressure source in response to remote user commands to effect the first and second end effector actions.

16. The system of claim 15 in which the at least one hydraulic pressure source comprises a remote hydraulic pressure.

17. The system of claim 15 in which the at least one hydraulic pressure source comprises a plurality of hydraulic pressure sources.

18. The system of claim 15 in which the controller is responsive to manual control or voice control commands or both.

19. The system of claim 15 in which the end effector includes a first actuator to effect the first action and a second actuator to effect the second action.

20. The system of claim 19 in which at least one of the actuators includes an expandable chamber.

* * * * *